United States Patent
Selimoglu-Buet et al.

(10) Patent No.: US 10,557,849 B2
(45) Date of Patent: Feb. 11, 2020

(54) DIAGNOSTIC OF CHRONIC MYELOMONOCYTIC LEUKEMIA (CMML) BY FLOW CYTOMETRY

(71) Applicant: INSTITUT GUSTAVE-ROUSSY, Villejuif (FR)

(72) Inventors: Dorothee Selimoglu-Buet, Issy les Moulineaux (FR); Orianne Wagner-Ballon (Epouse Terrazzoni), Sceaux (FR); Eric Solary, Paris (FR); Nathalie Droin, Villejuif (FR)

(73) Assignee: INSTITUT GUSTAVE-ROUSSY, Villejuif (FR)

( * ) Notice: Subject to any disclaimer, the term of this patent is extended or adjusted under 35 U.S.C. 154(b) by 205 days.

(21) Appl. No.: 15/312,746

(22) PCT Filed: Mar. 31, 2015

(86) PCT No.: PCT/EP2015/057135
§ 371 (c)(1),
(2) Date: Nov. 21, 2016

(87) PCT Pub. No.: WO2015/176860
PCT Pub. Date: Nov. 26, 2015

(65) Prior Publication Data
US 2017/0184598 A1    Jun. 29, 2017

(30) Foreign Application Priority Data

May 22, 2014   (EP) .................................... 14305755

(51) Int. Cl.
*G01N 33/574*   (2006.01)
*G01N 33/50*    (2006.01)

(52) U.S. Cl.
CPC ... *G01N 33/57426* (2013.01); *G01N 33/5044* (2013.01); *G01N 33/5047* (2013.01); *G01N 33/5055* (2013.01); *G01N 33/57492* (2013.01); *G01N 2800/52* (2013.01)

(58) Field of Classification Search
CPC ......... G01N 33/57426; G01N 33/5047; G01N 33/57492; G01N 33/5044; G01N 33/5055; G01N 2800/52
See application file for complete search history.

(56) References Cited

FOREIGN PATENT DOCUMENTS

WO   WO 2013/139479 A1   9/2013

OTHER PUBLICATIONS

Zawada et al. SUperSAGE evidence for CD14++CD16+ monocytes as a third monocyte subset. Blood. 118 (12): e50-e61 (2011)).*

(Continued)

*Primary Examiner* — Gailene Gabel
(74) *Attorney, Agent, or Firm* — Potomac Law Group, PLLC

(57) ABSTRACT

The present invention relates to an in vitro method of diagnosing chronic myelomonocytic leukemia (CMML) in a subject, said method comprising the steps of: a) Detecting a monocyte population in a biological sample from said subject; b) Quantifying the CD14+/CD16− monocytes in said biological sample; c) Comparing the value of step b) to a reference value; and d) Diagnosing CMML based on said comparison. Preferably, said detecting step a) is performed by an exclusion gating strategy by flow cytometry.

Figure 1:
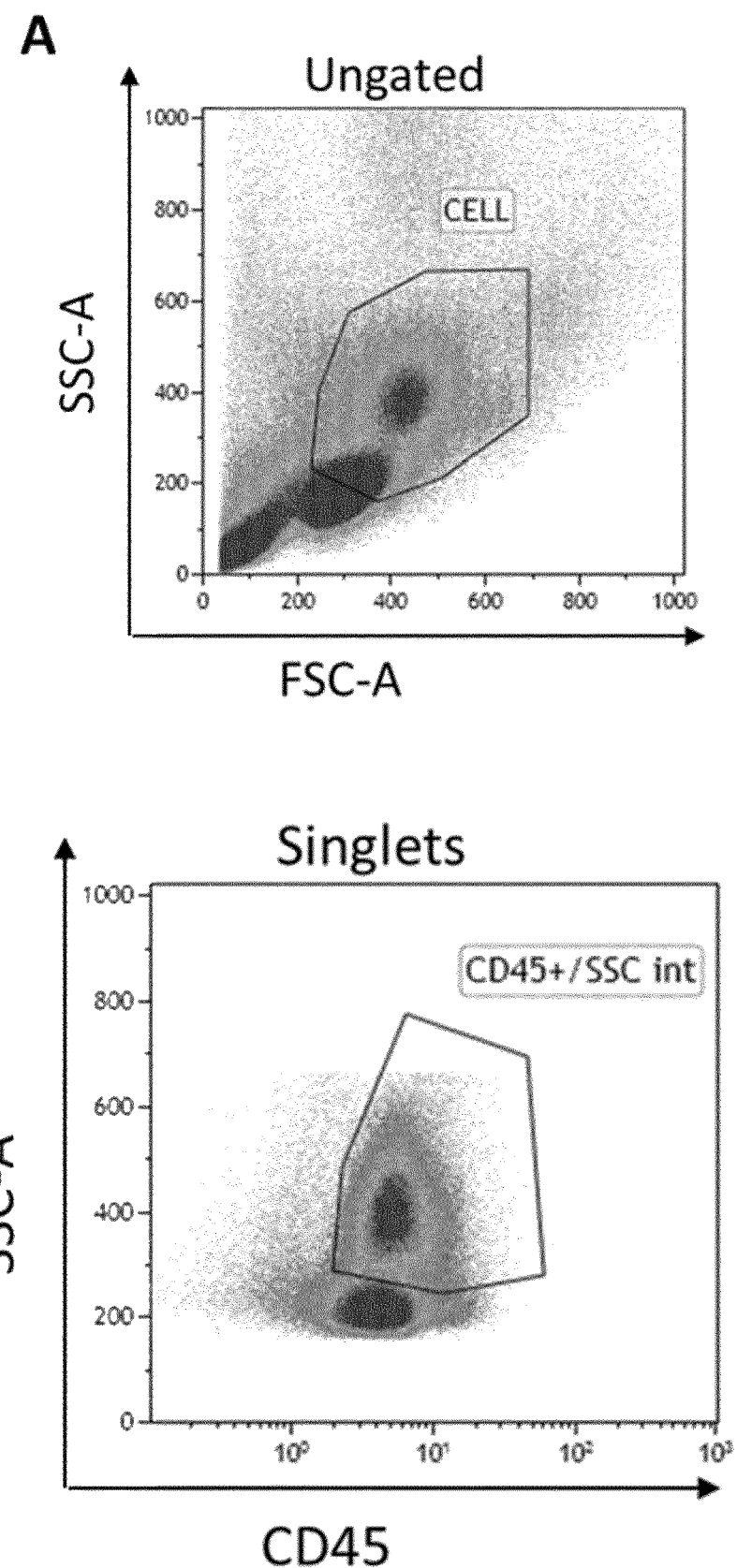

4 Claims, 21 Drawing Sheets
Specification includes a Sequence Listing.

(56) References Cited

OTHER PUBLICATIONS

Qubaja et al. The detection of CD14 and CD16 in paraffin-embedded bone marrow biopsies is useful for the diagnosis of chronic myelomonocytic leukemia. Vhirchow Arch 454: 411-419 (2009).*

Xu et al. Flow Cytometric Analysis of Monocytes as a Tool for Distinguishing Chronic Myelomonocytic Leukemia from Reacrive Monocytosis. Am J. Clin. Pathol. 124: 799-806 (2005).*

Droin et al. Alpha-defensins secreted by dysplastic granulocytes inhibit the differentiation of monocytes in chronic myelomonocytic leukemia. Blood. 115(1): 78-88 (2010).*

Xu et al. Flow Cytometric Analysis of Monocytes as a Tool for Distinguishing Chronic Myelomonocytic Leukemia From Reactive Monocytosis. Am. J. Clin. Pathol. 124: 799-806 (2005).*

Casolari et al. Monocytes between reactivity and dysplasia. Haematologica vol. 94, Suppl 4, pp. 79. Abstract (Oct. 2009).*

Droin et al., "Alpha-defensins secreted by dysplastic granulocytes inhibit the differentiation of monocytes in chronic myelomonoctic leukemia," Blood, vol. 115, No. 1, pp. 78-88, Jan. 2010.

European Search Report for European Application No. 14305755 dated Nov. 27, 2014.

Fleit et al., "A Common Epitope is Recognized by Monoclonal Antibodies Prepared against Purified Human Neutrophil FcyRIII (CD16)," Clinical Immunology and Immunopathology, vol. 62, No. 1, pp. 16-24, Jan. 1992.

Fleit, Monoclonal Antibodies to Human Neutrophil FcyRIII (CD16) Identify Polypeptide Epitopes, Clinical Immunology and Immunopathology, vol. 59, pp. 232-235, 1991.

Lacronique-Gazaille et al., "A simple method for detection of major phenotypic abnormalities in myelodysplastic syndromes: expression of CD56 in CMML," Haematologica, vol. 92, pp. 859-860, 2007.

Onida et al., "Prognostic factors and scoring systems in chronic myelomonocytic leukemia: a retrospective analysis of 213 patients," Blood, vol. 99, No. 3, pp. 840-849, Feb. 2002.

Tamm et al., "The binding epitopes of human CD16 (Fc gamma RIII) monoclonal antibodies. Implications for ligand binding," The Journal of Immunology, vol. 157, pp. 1576-1581, 1996.

Vardiman et al., "The 2008 revision of the World Health Organization (WHO) classification of myeloid neoplasms and acute leukemia: rationale and important changes," Blood, vol. 114, No. 5, pp. 937-951, Jul. 2009.

Wong et al., "Gene expression profiling reveals the defining features of the classical, intermediate, and nonclassical human monocyte subsets," Blood, vol. 118, No. 5, pp. e16-e31, Aug. 2011.

Zawada et al., "SuperSAGE evidence for CD14++CD16+ monocytes as a third monocyte subset," Blood, vol. 118, No. 12, pp. e50-e61, Sep. 2011.

Ziegler-Hoitbrock et al., "Nomenclature of monocytes and dendritic cells in blood," Blood, vol. 116, No. 16, pp. e74-e80, Oct. 2010.

Qubaja et al., "The detection of CD14 and CD16 in paraffin-embedded bone marrow biopsies is useful for the diagnosis of chronic myelomonocytic leukemia," Virchows Archiv, vol. 454, No. 4, pp. 411-419, Feb. 2009.

Xu et al., "Flow Cytometric Analysis of Moncytes as a Tool for Distinguishing Chronic Myelomonocytic Leukemia From Reactive Monocytosis," American Journal of Clinical Pathology, vol. 124, No. 5, pp. 799-806, Nov. 2005.

Vukovic et al., "Dendritic cells in chronic myelomoncytic leukaemia," British Journal of Hawmatology, vol. 105, No. 4, pp. 974-985, Jun. 1999.

Rollins-Raval et al., "The value of immunohistochemistry for CD14, CD123, CD33, myeloperoxidase, and CD68R in the diagnosis of acute and chronic myelomonocytic leukaemias," Histopathology, vol. 60, No. 6, pp. 933-942, Feb. 2012.

Moestrup et al., "Surface expression of the alpha2-macroglobulin receptor on human malignant blood cells," Leukemia Research, vol. 16, No. 3, pp. 227-234, Mar. 1992.

International Search Report issued in application No. PCT/EP2015/057135 dated Jun. 10, 2015.

* cited by examiner

FIGURE 1 (CONTINUATION)
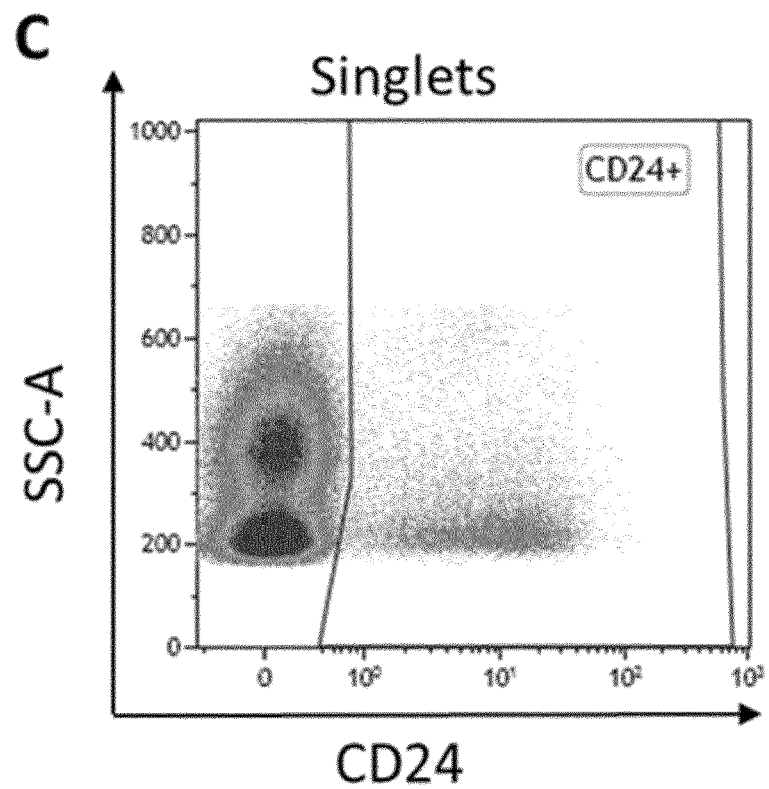
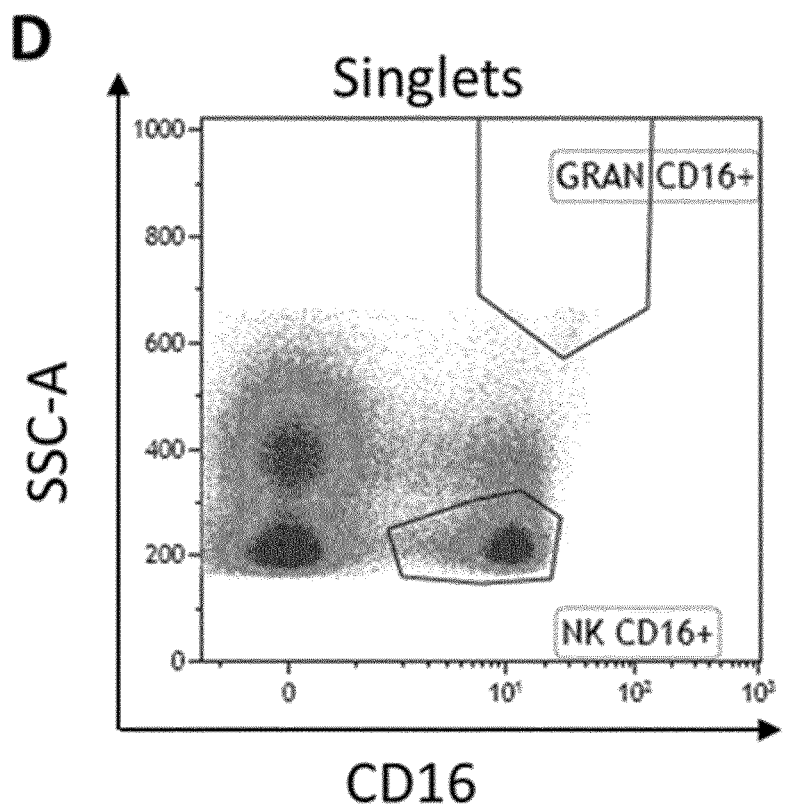

FIGURE 1 (CONTINUATION)
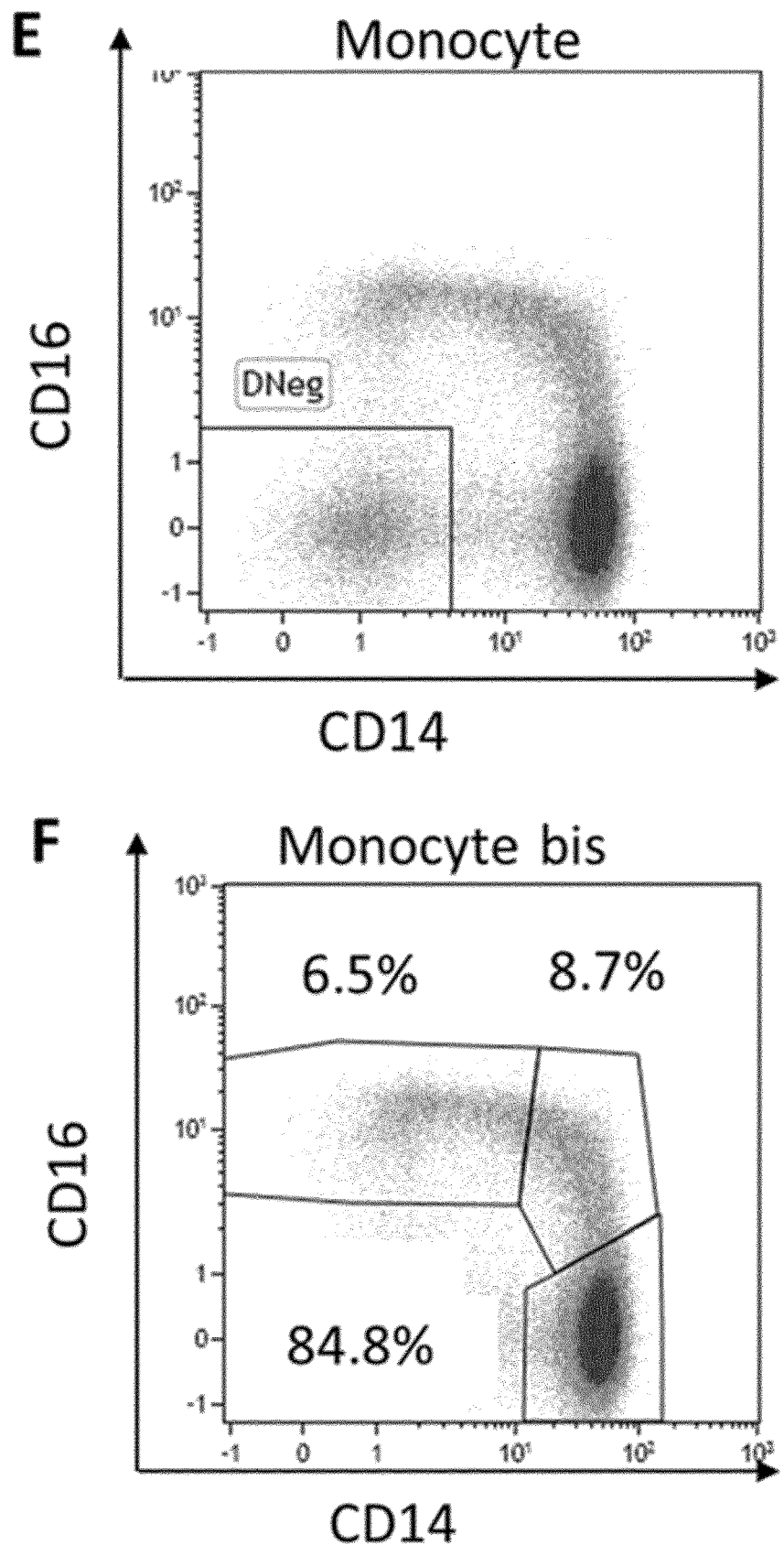

Figure 2:
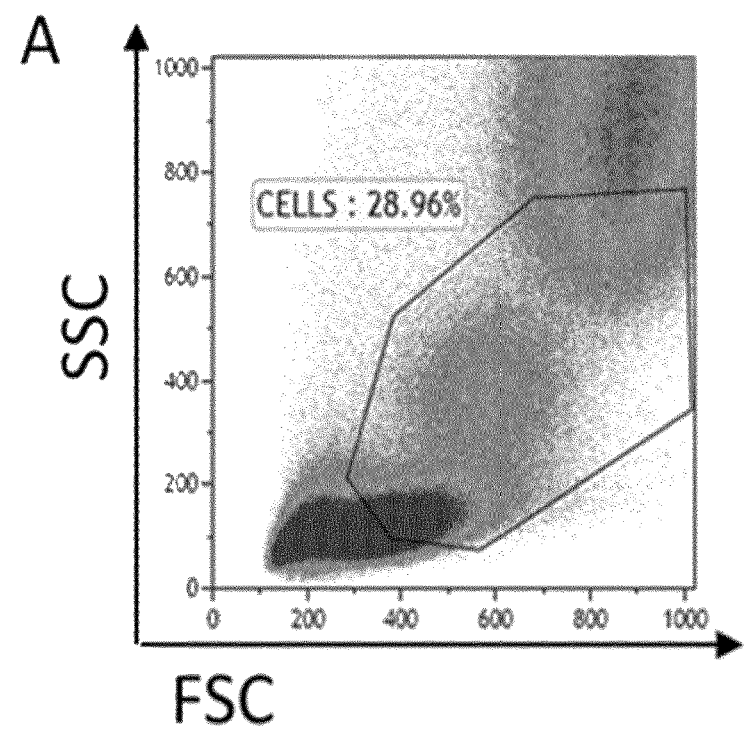
Figure 2:
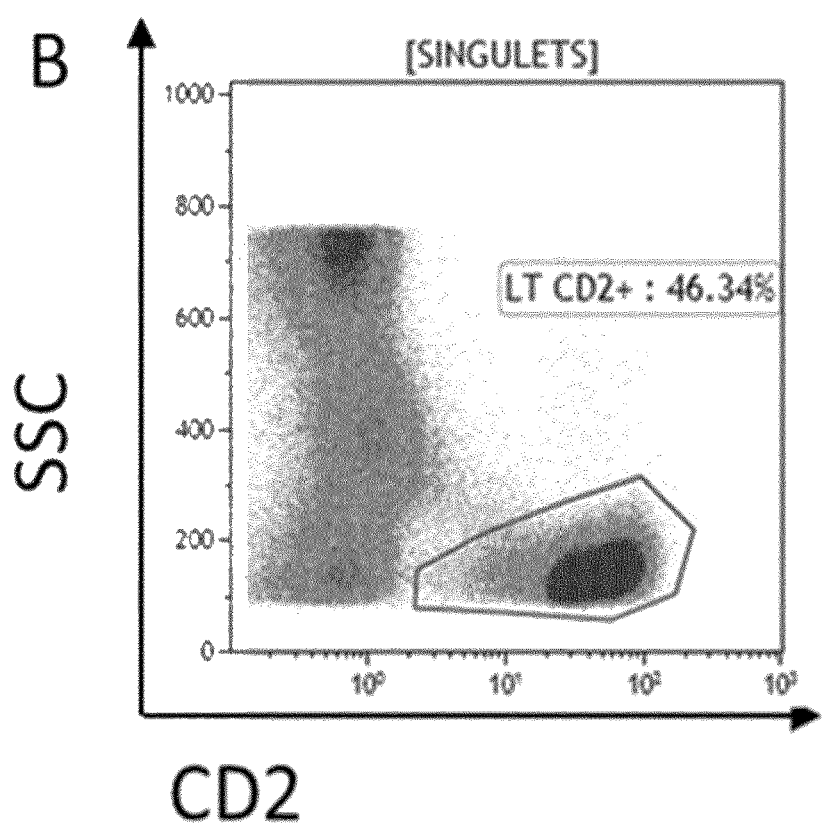

FIGURE 2 (CONTINUATION)
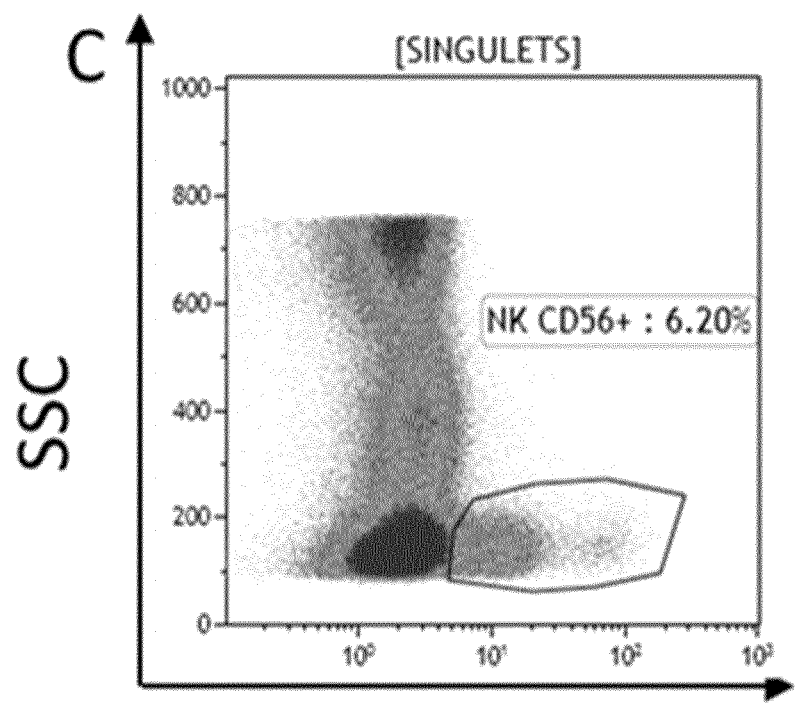
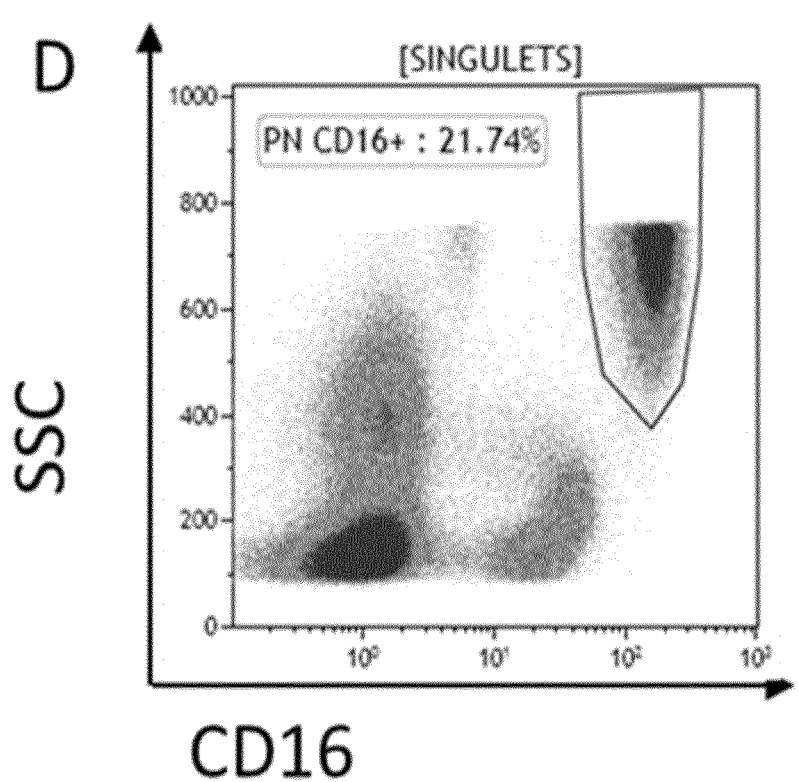

FIGURE 2 (CONTINUATION)
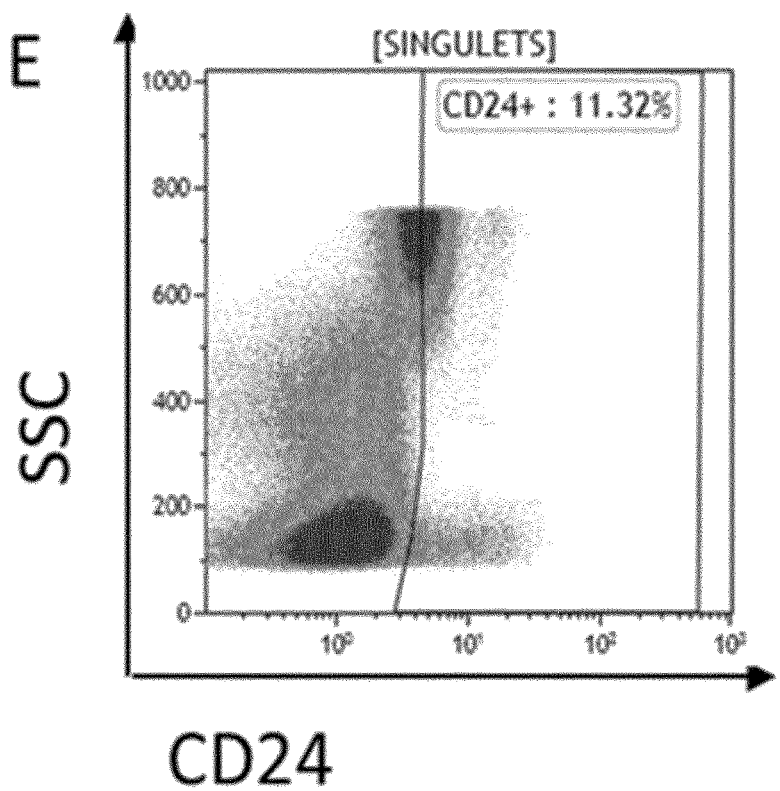
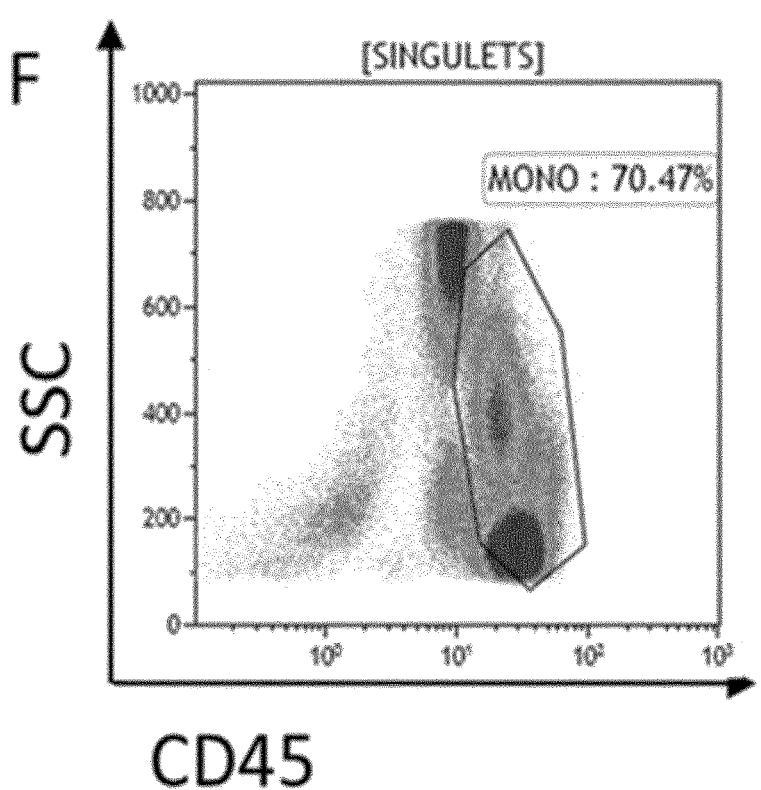

FIGURE 2 (CONTINUATION)
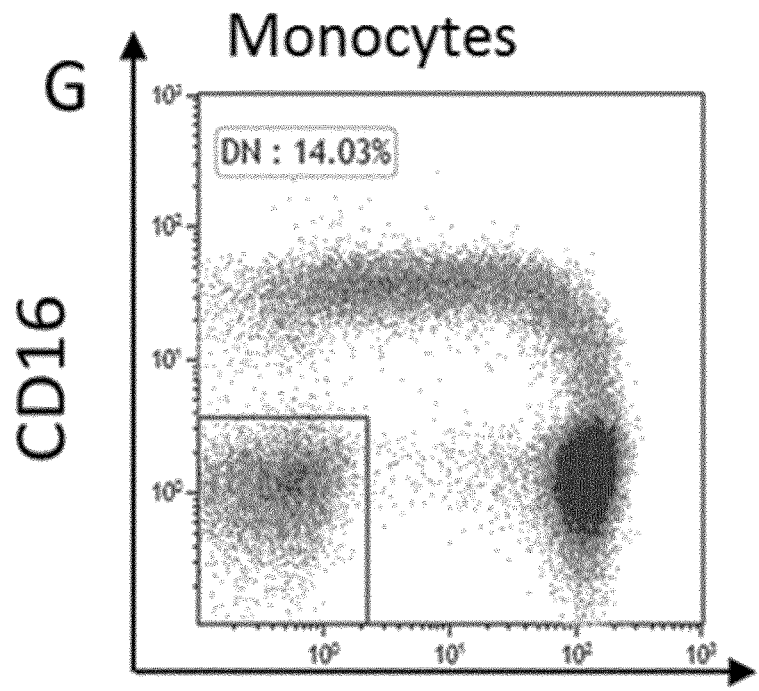
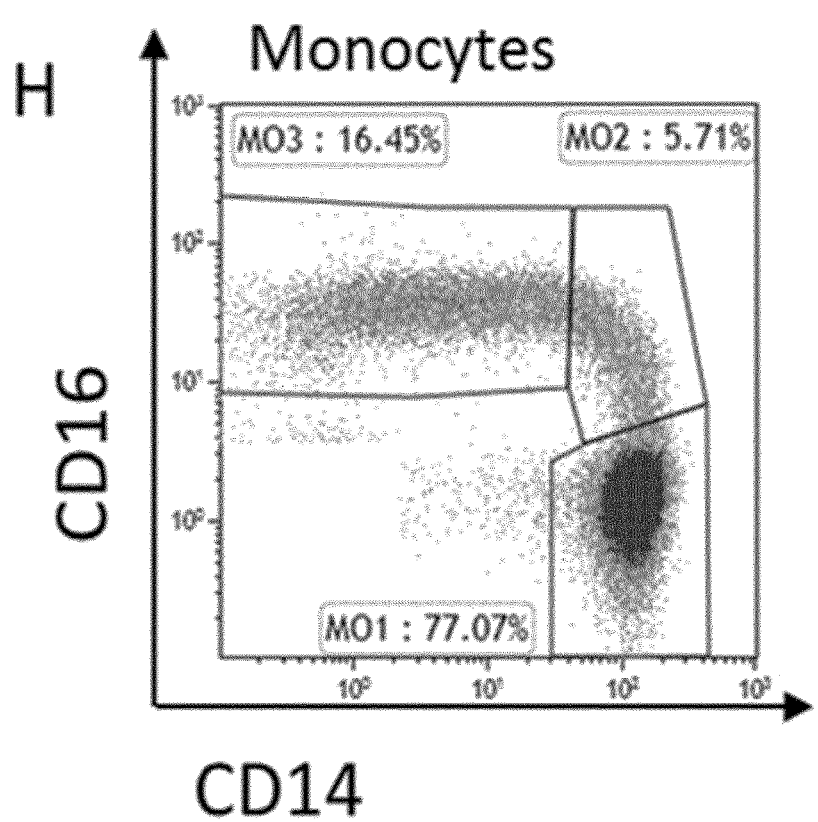

Figure 3:
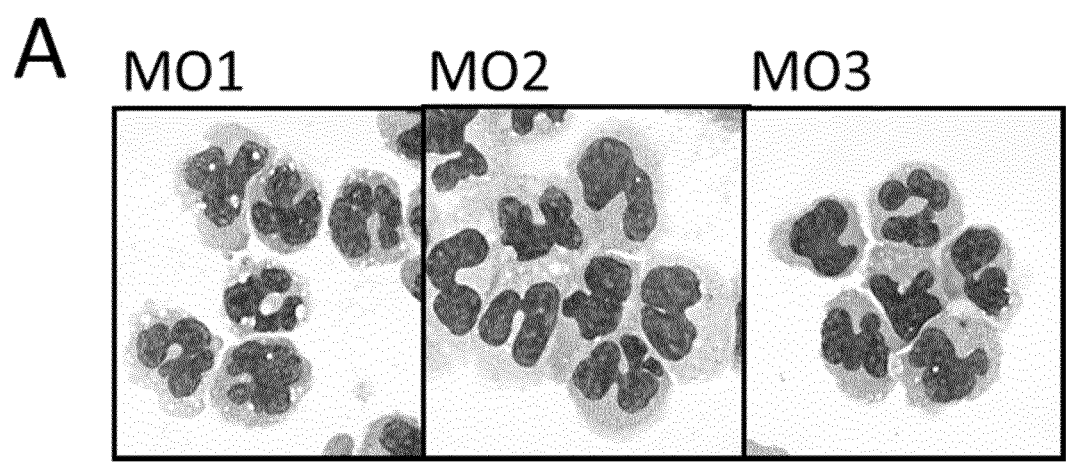

FIGURE 3 (CONTINUATION)
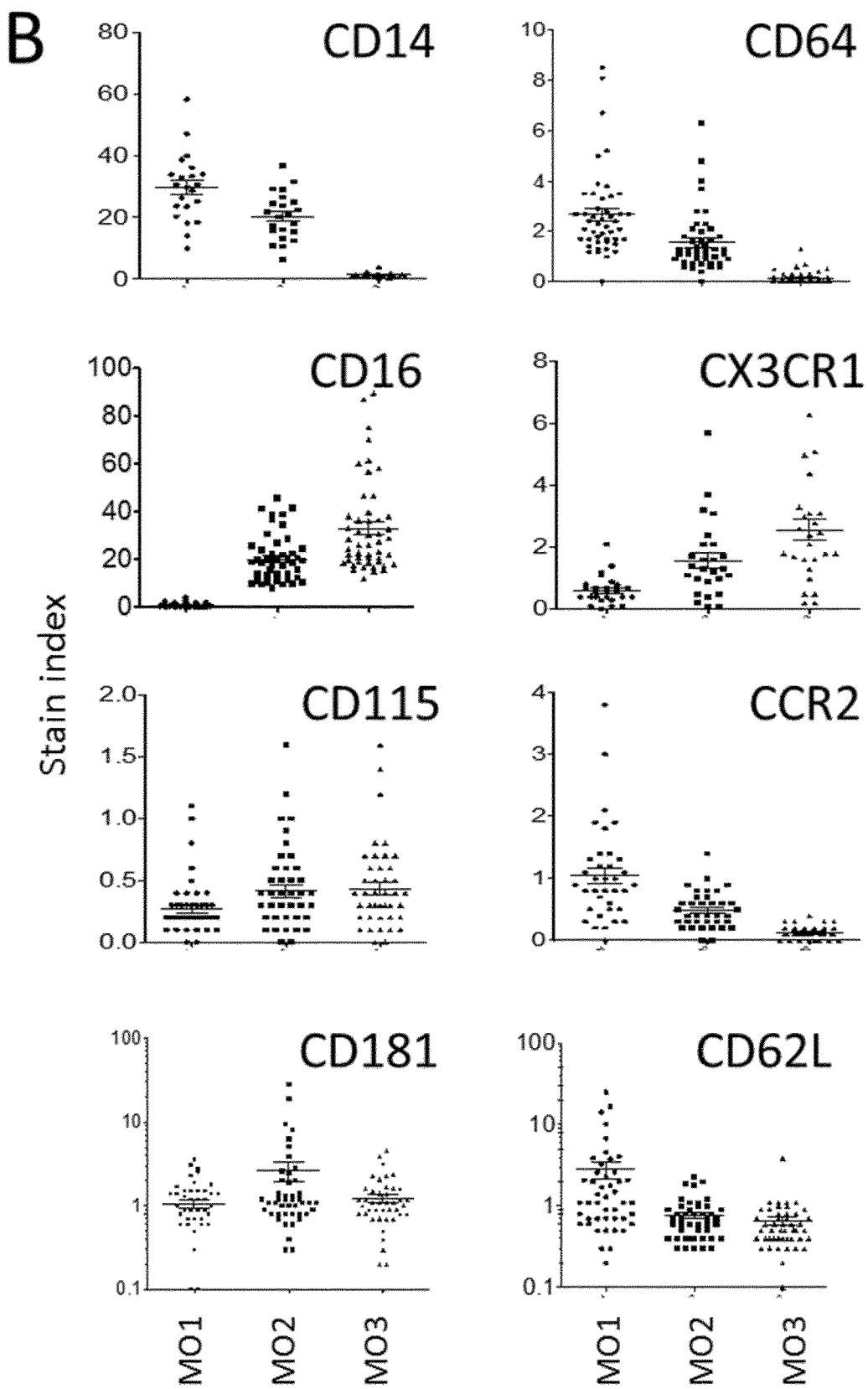

FIGURE 3 (CONTINUATION)
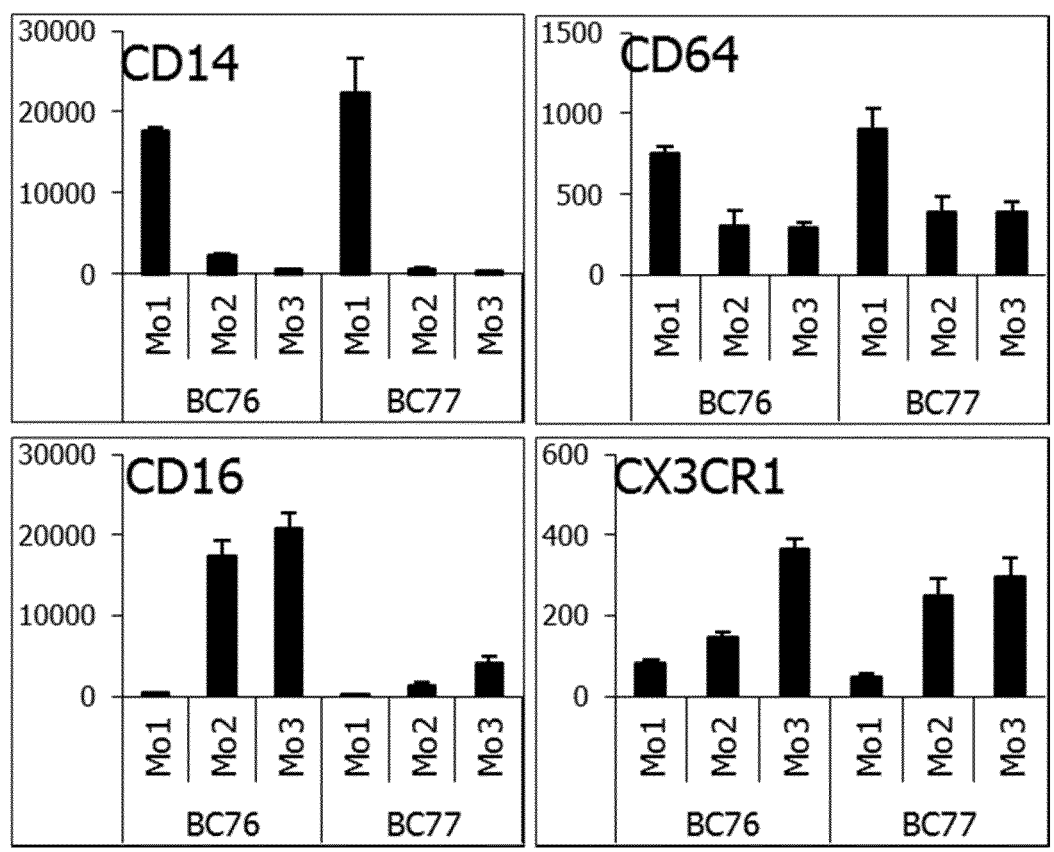

Figure 4:
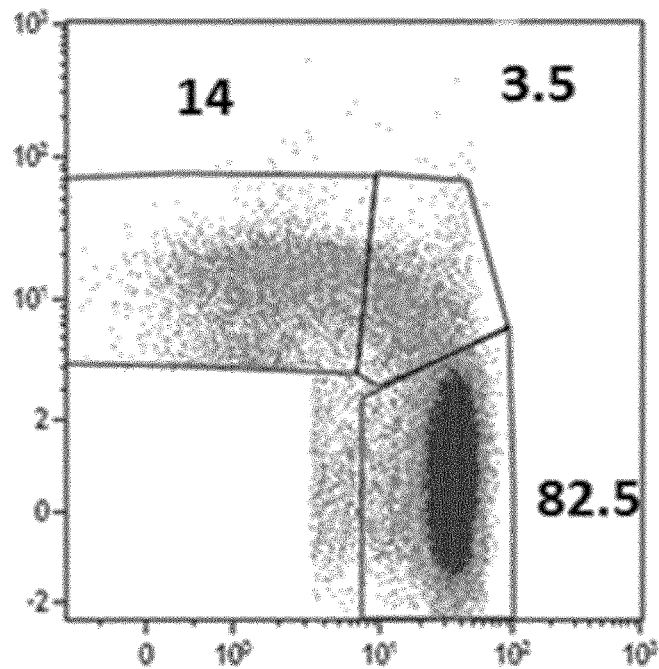
Figure 4:
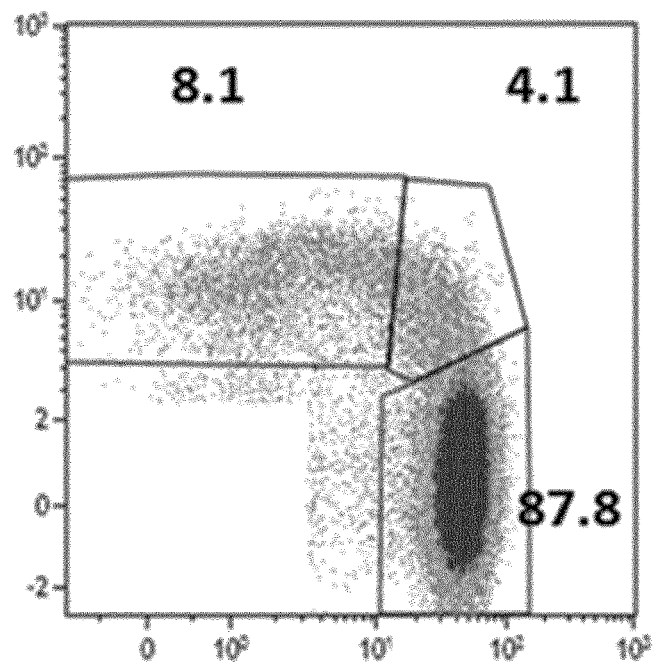

FIGURE 4 (CONTINUATION)
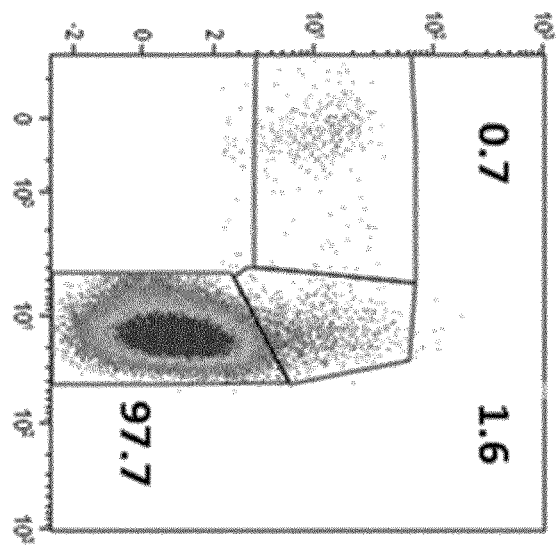
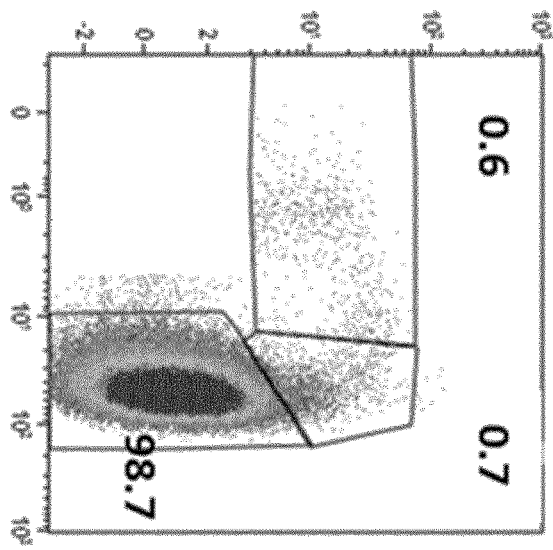
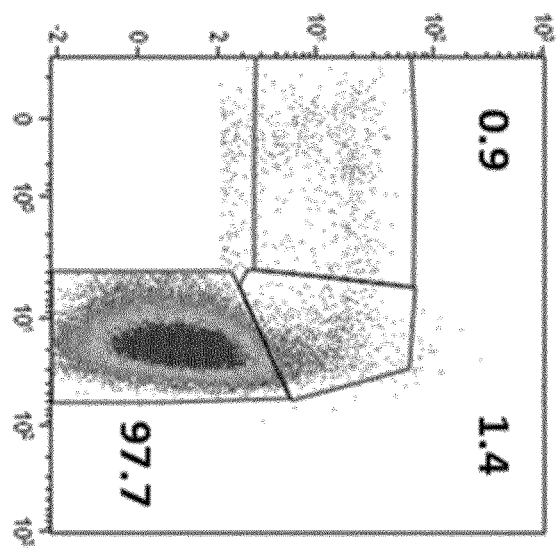

FIGURE 4 (CONTINUATION)
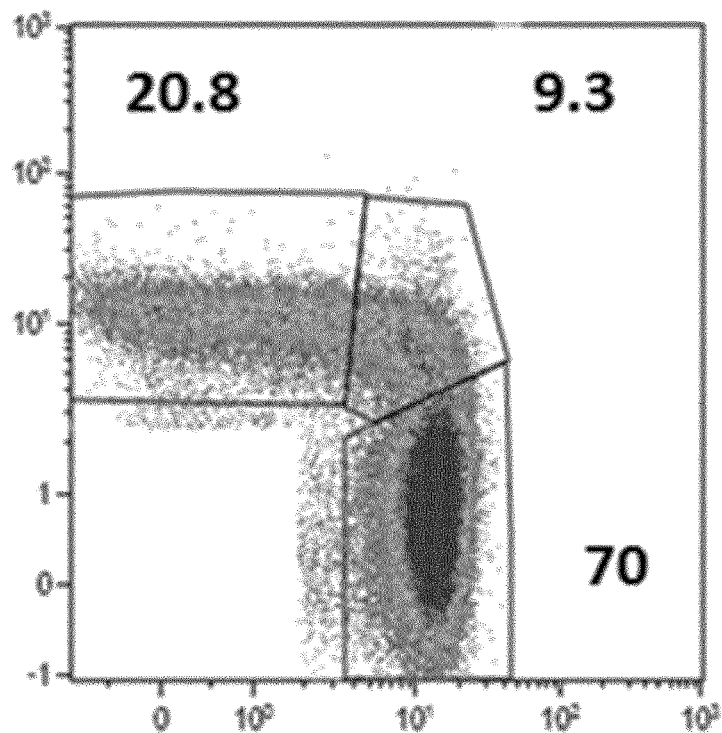
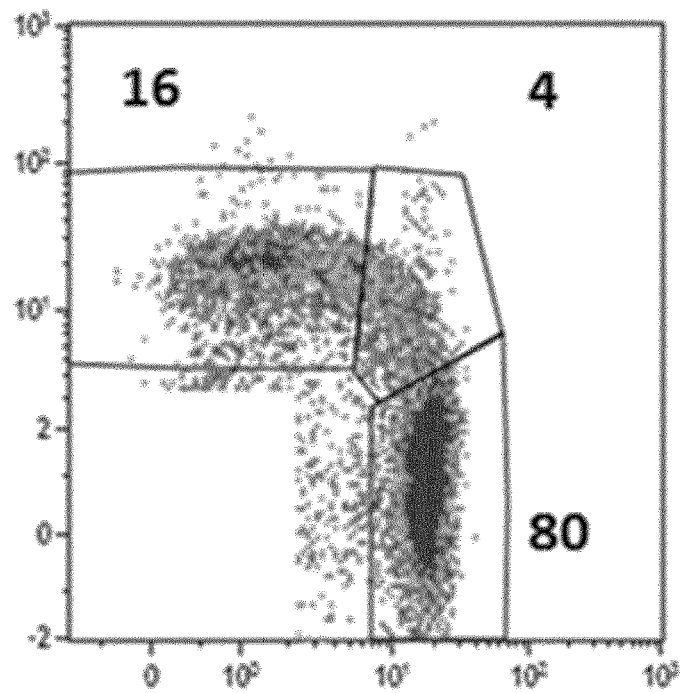

FIGURE 4 (CONTINUATION)
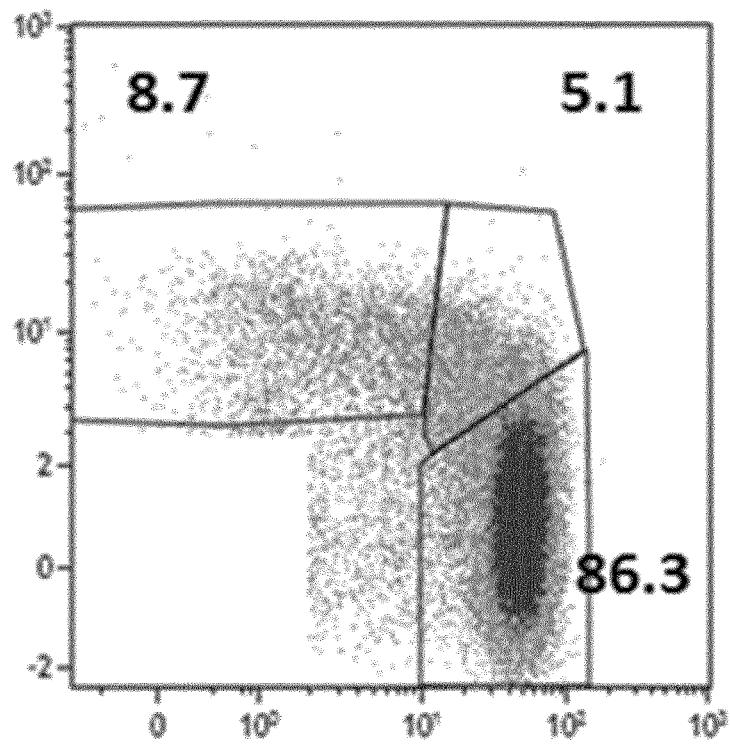
F MPN (PV)
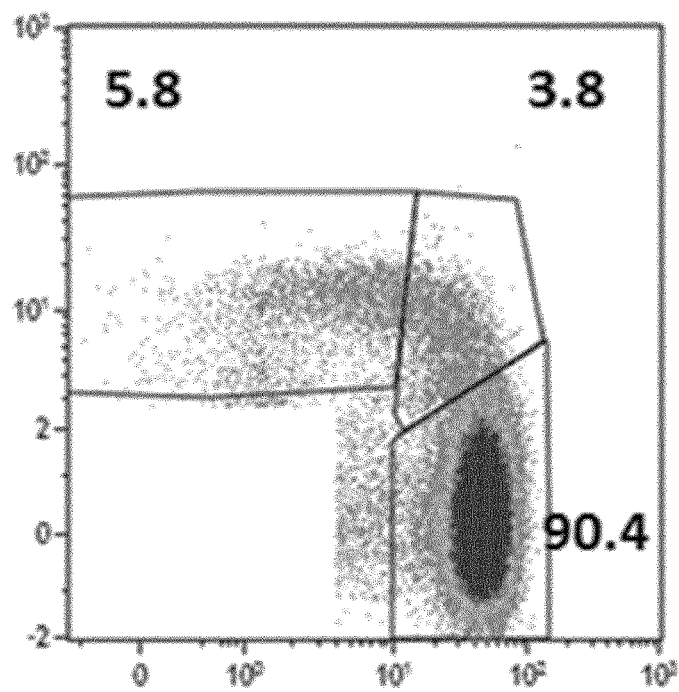
G MPN (At.)

FIGURE 4 (CONTINUATION)
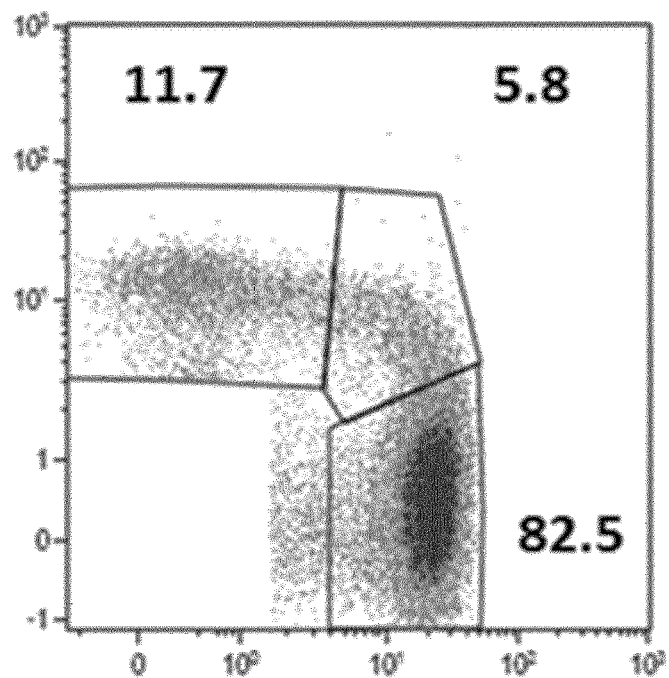
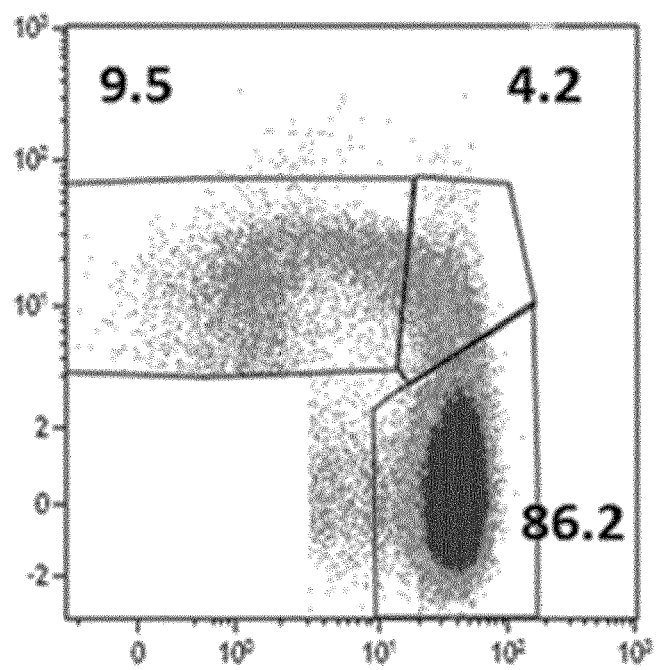

FIGURE 4 (CONTINUATION)
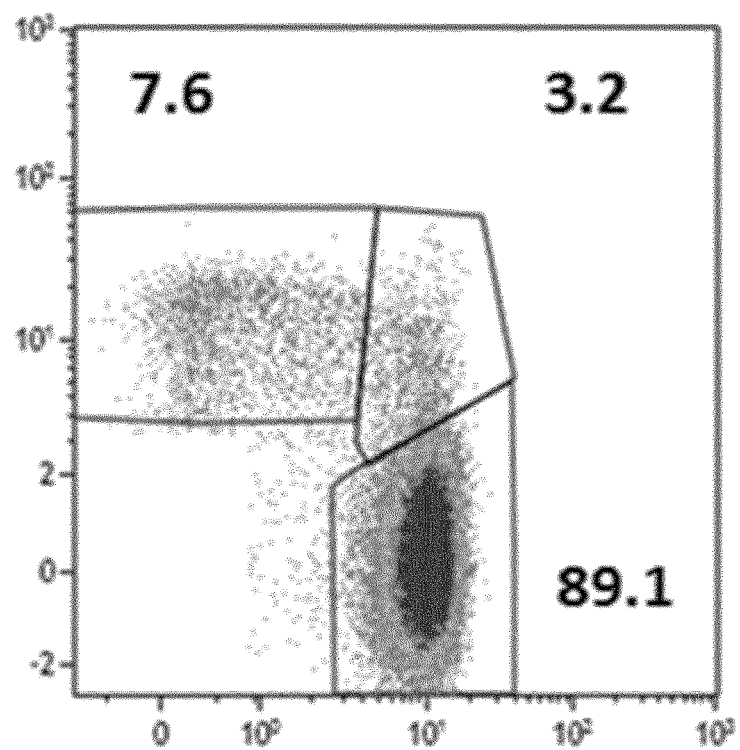
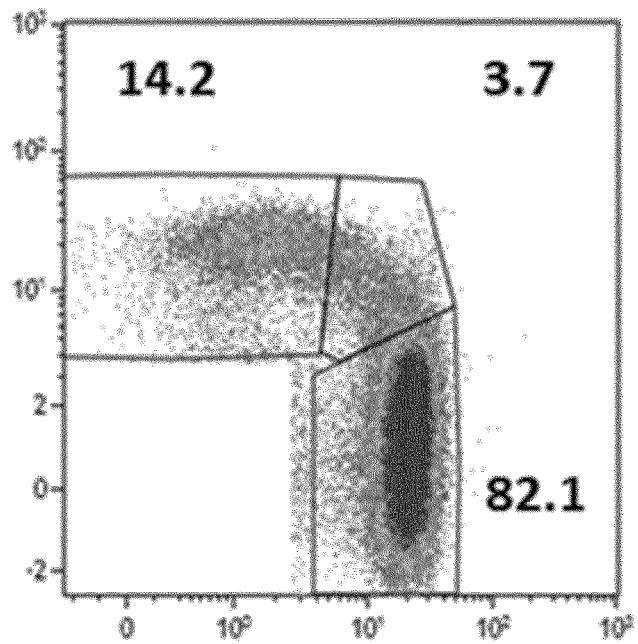

A

Figure 5:
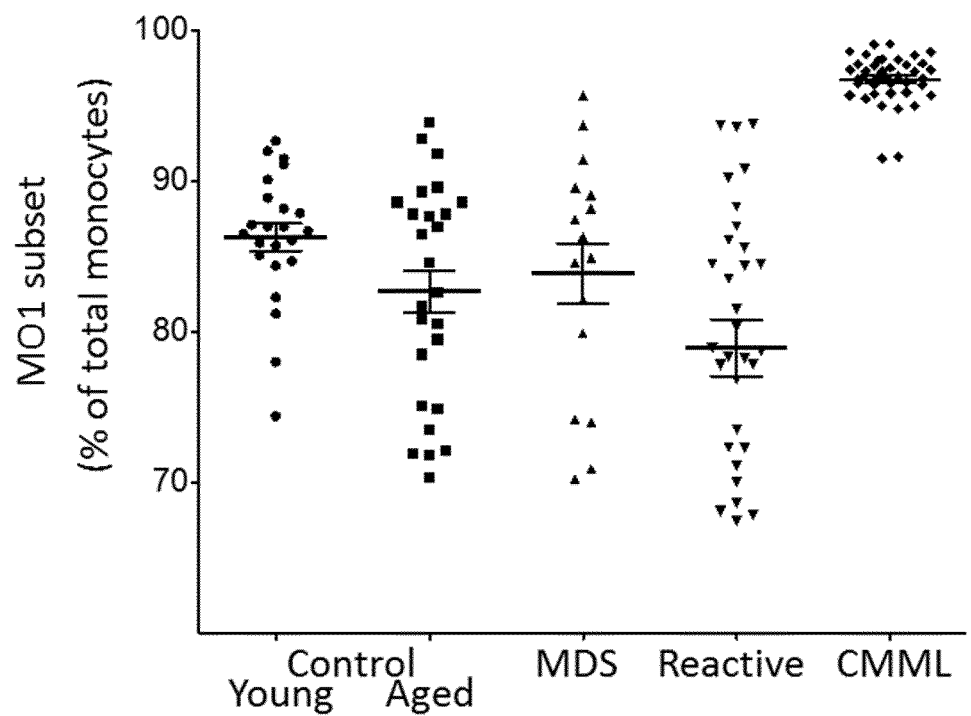
Figure 5:
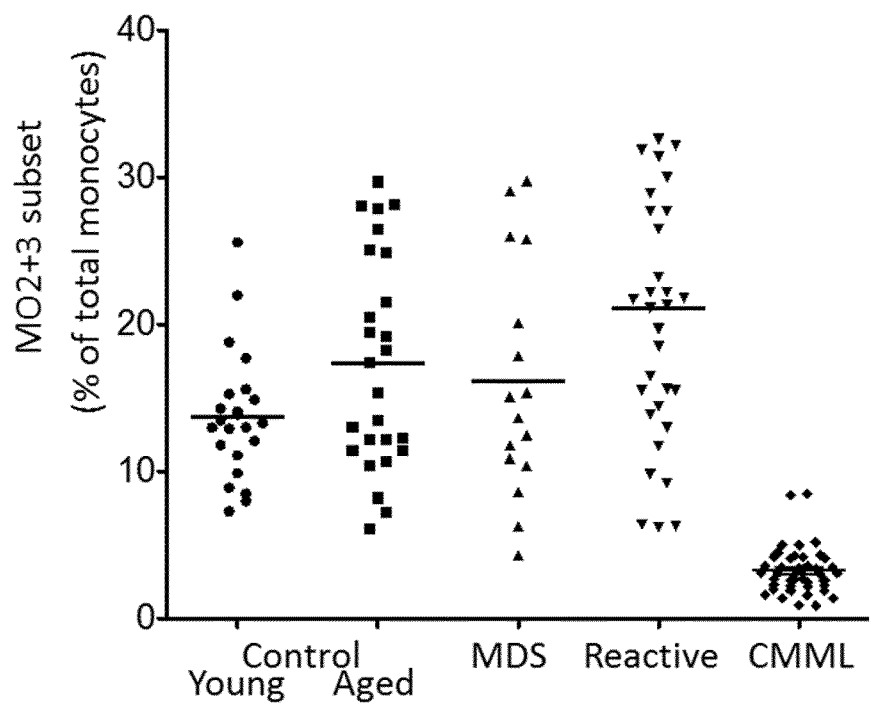

FIGURE 5 (CONTINUATION)
B
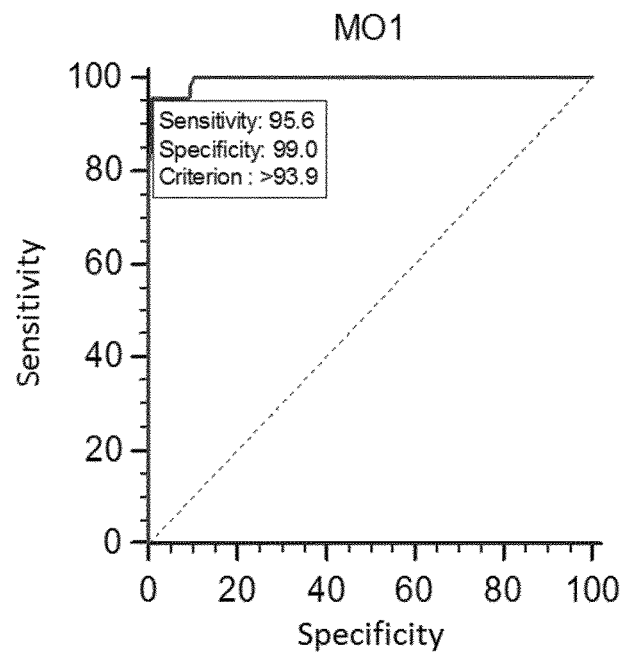
C
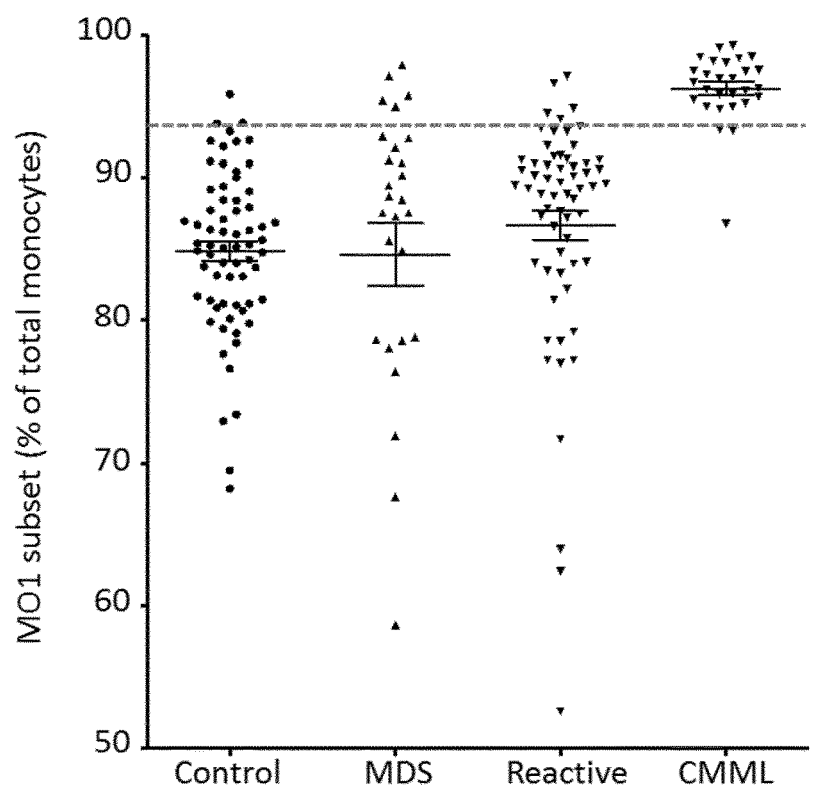

A

Before treatment

Responders
(range mono <1)

After treatment

Responders
(range mono <1)

Figure 6:
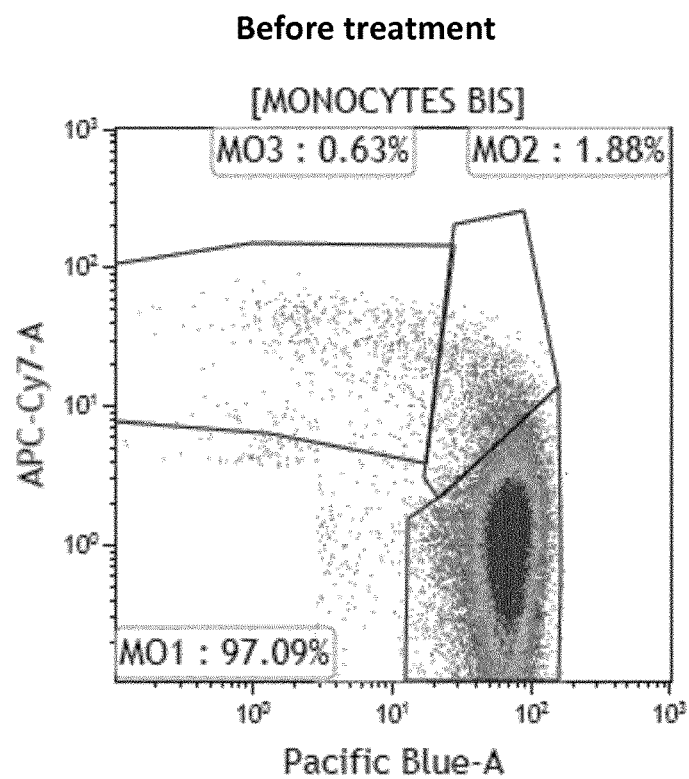
Figure 6:
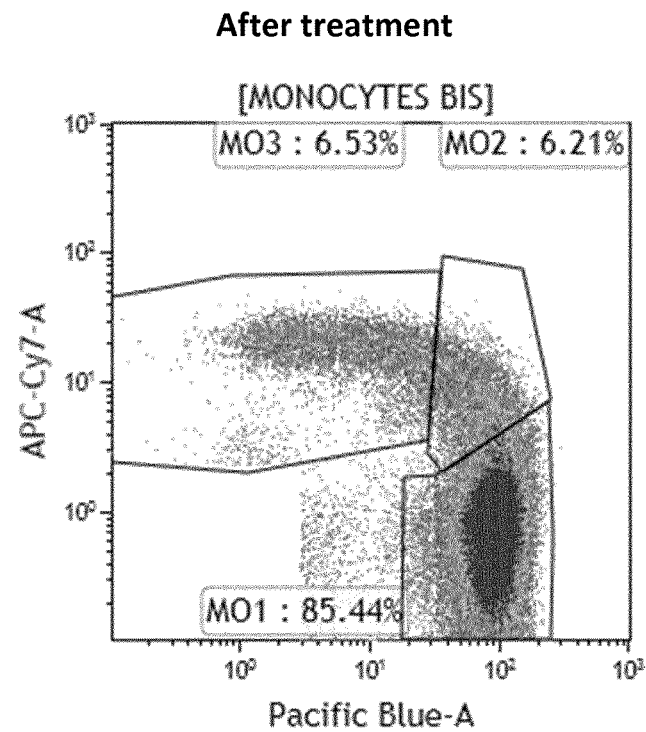

FIGURE 6 (CONTINUATION)
B
No Responders
(taux mono >1)
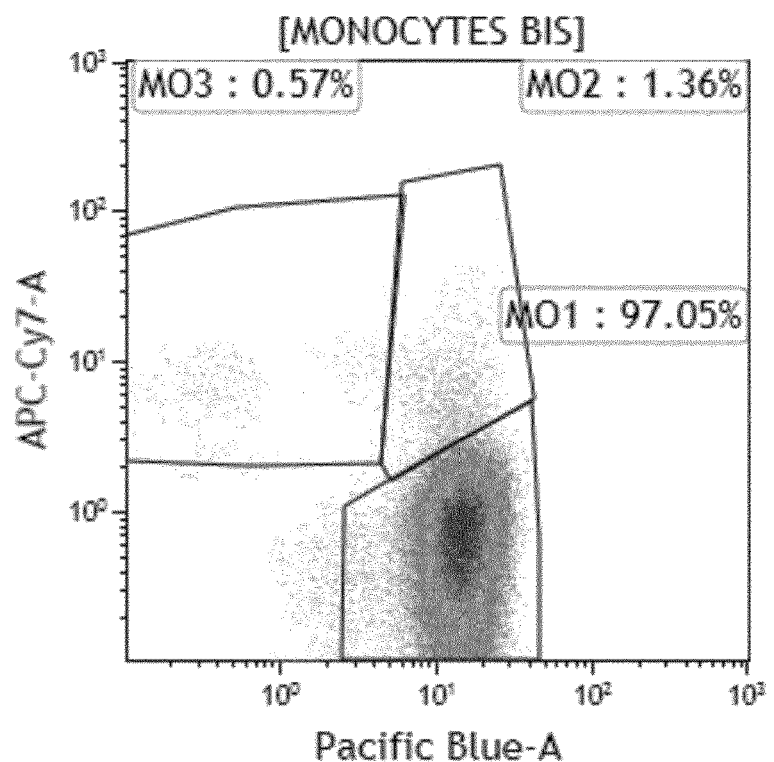
No Responders
(taux mono >1)
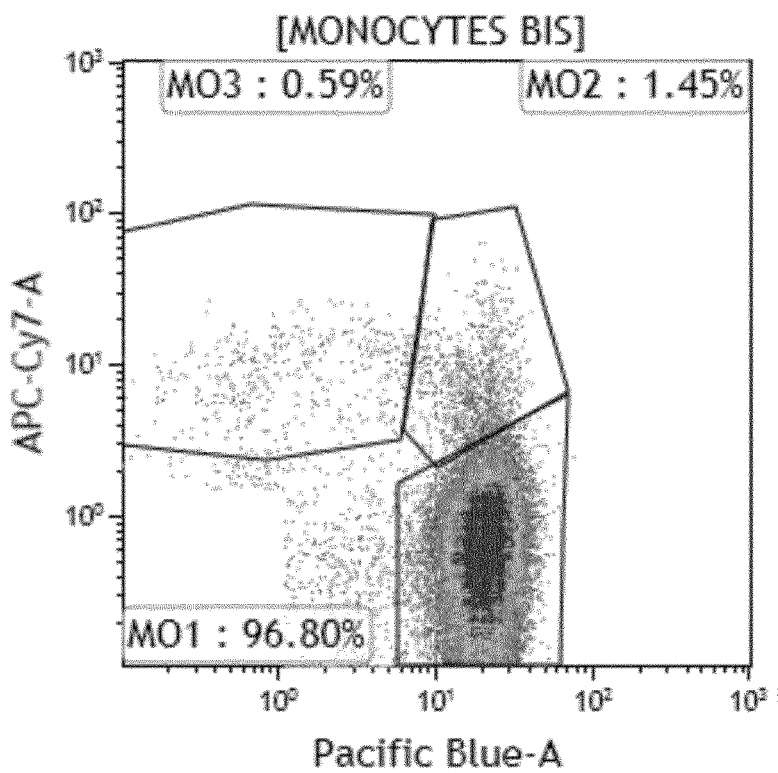

A

B

DIAGNOSTIC OF CHRONIC MYELOMONOCYTIC LEUKEMIA (CMML) BY FLOW CYTOMETRY

BACKGROUND OF THE INVENTION

Hematopoiesis is maintained by a hierarchical system where hematopoietic stem cells (HSCs) give rise to multipotent progenitors, which in turn differentiate into all types of mature blood cells. Clonal stem-cell disorders in this system lead to Acute Myeloid Leukemia (AML), Myeloproliferative Neoplasms (MPNs), Myelodysplastic Syndromes (MDS) and Myelodysplastic/Myeloproliferative disorders.

Among these disorders, myelodysplastic/myeloproliferative neoplasms include four myeloid diseases grouped in 1999 by the WHO: chronic myelomonocytic leukemia (CMML), juvenile myelomonocytic leukemia (JMML), atypical chronic myeloid leukemia (aCML) and unclassified myelodysplastic/myeloproliferative syndromes (U-MDS/MPS) (Vardiman et al., Blood 114:937-951, 2009).

CMML is a rare disorder with an estimated incidence of 1 case per 100 000 persons per year. Median age at presentation is 70 years, and presenting manifestations may include those of bone marrow failure and systemic symptoms. Hepatomegaly and splenomegaly are found in some patients, and the white blood cell count is typically increased.

The current diagnosis of CMML relies on the criteria defined by WHO in 2008 (Vardiman et al., Blood 114:937-951, 2009). CMML definition is based on only one positive criterion, which is the elevation of monocytes to more than $1\times10^9$/L, measured over at least 3 months. Negative criteria exclude i) acute leukemia by cytological examination of the blood and bone marrow showing a percentage of blast cells lower than 20%, ii) chronic myeloid leukemia by demonstrating the lack of BCR-ABL fusion gene, and iii) the so-called Myeloid and Lymphoid Neoplasms with Eosinophilia (MLN-Eo) when eosinophilia is combined with monocytosis by checking the lack of gene rearrangement involving a PDGFR (Platelet-Derived Growth Factor Receptor) or FGFR (Fibroblast Growth Factor Receptor) gene.

However, some patients with myelofibrosis (MF) in proliferative phase and some patients with chronic inflammatory disease or late stage metastatic solid tumor and reactive monocytosis, meet this criteria, whereas patients with dysplastic CMML and low white blood cell (WBC) count and so less than $1\times10^9$/L of monocytes, do not. The differentiation with unclassified MDS/MPN can thus be problematic. Genetic analyses failed to identify a specific cytogenetic or genetic abnormality in CMML, although a characteristic molecular fingerprint based on the high frequency of mutations in TET2, SRSF2 and ASXL1 genes, has been established.

Additional efforts are needed to improve the disease definition and facilitate its rapid and accurate identification in daily clinical practice. Thus there is still a need for a new diagnosis method of CMML which is rapid, efficient and simple.

FIGURES

FIG. 1: Overview of the gating strategy for human monocyte subsets analysis in PBMC by flow cytometry. (A) Monocytes selection based on morphological parameters (FSC versus SSC). (B) Monocytes defined as CD45$^+$/SSC intermediate cells. (C) Granulocytes and B cells selected as CD24$^+$ cells. (D) Isolated CD16$^{high}$ granulocytes (PMN) and NK cells. (E) CD16 and CD14 staining. (F) Identification of the three monocytes subsets: CD14$^+$ CD16$^-$ (classical), CD14$^+$ CD16$^+$ (intermediate) and CD14$^{low}$ CD16$^+$ (non classical) monocytes.

FIG. 2: Overview of the exclusion gating strategy for human monocyte subsets analysis in total blood cells by flow cytometry. A) Monocytes selection on morphological parameters (FSC versus SSC). (B) Selection of CD2$^+$ T cells. (C) NK cells as CD56$^+$ cells. (D) Isolated CD16$^{high}$ granulocytes (PMN). (E) Selection of B cells and granulocytes as CD24$^+$ cells. (F) Monocyte population obtained on CD45 SSC dot-plot as CD45$^+$/SSC intermediate. (G) CD16 and CD14 staining (H) Identification of the three monocytes subsets: CD14$^+$ CD16$^-$ (classical), CD14$^+$ CD16$^+$ (intermediate) and CD14$^{low}$ CD16$^+$ (non classical) monocytes.

FIG. 3: Monocytes population characterization. (A) MGG cytospin preparation of sorted monocytes according to their CD14 and CD16 expression profile. (B) Box plots showing surface marker expression, as stain index=(Median of Monocyte population−Median of Lymphocyte population (as negative peak))/2×standard deviation of negative peak) in different monocyte subsets in healthy donors (young and age-matched controls). Different scales were used for different markers. (C) RT-PCR.

FIG. 4: Representation of monocyte subsets from blood of (A) young controls, (B) aged-match controls, (C) CMML or (D, E, F, G, H, I, J, K) various hemopathies by flow cytometry based on CD14 and CD16 expression. Numbers depict percentage of distinct monocyte subsets.

FIG. 5: Analysis of MO1 population in learning and validation cohort. (A) Dot plot of classical monocytes percentage (MO1) (upper panel) and the "intermediate" monocyte (MO2) and the "non-classical" monocyte (MO3) (lower panel) for learning cohort. Black line represents mean±SEM. (B) Receiver operating characteristic (ROC) curve analysis of diagnostic sensitivity and specificity of the MO1 percentage in blood. (C) Dot plot of classical monocytes percentage (MO1) for validation cohort. Black line represents mean±SEM.

FIG. 6: Representation of monocyte subsets from blood of (A) Responders and (B) No responders, by flow cytometry based on CD14 and CD16 expression. Numbers depict percentage of distinct monocyte subsets.

Figure 7:
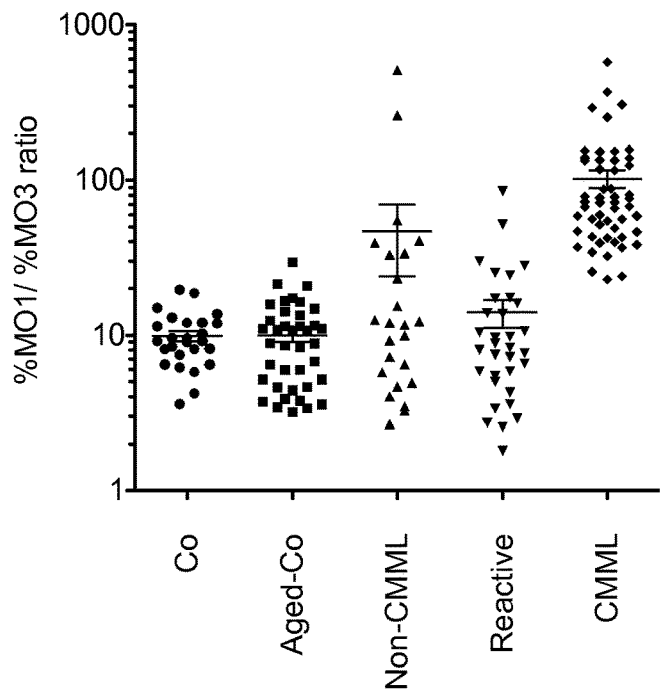
Figure 7:
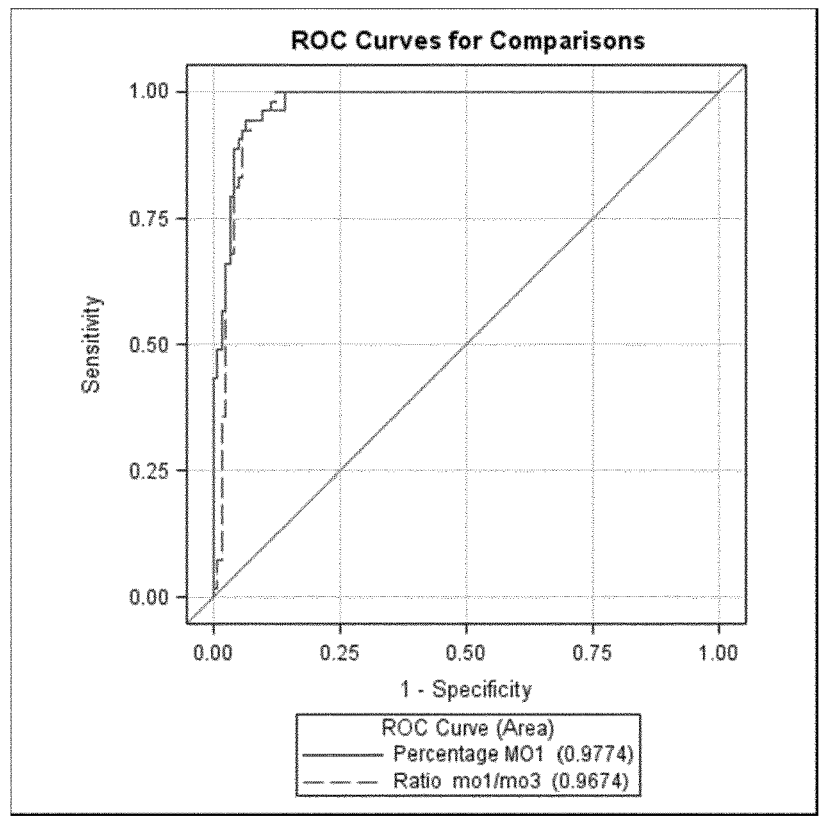

FIG. 7: Representation of the MO1/MO3 ratio for the learning cohort. (A) Percentage of MO1/MO3 monocytes in a learning cohort of CMML compared to healthy blood donors (Co), age-matched healthy donors (Aged-Co), patients with diverse hematological malignancies (non-CMML) and those with a reactive monocytosis (reactive). (B) Receiver operating characteristic (ROC) curve analysis of diagnostic sensitivity and specificity of the MO1/MO3 percentage in blood.

DETAILED DESCRIPTION

Unless specifically defined, all technical and scientific terms used herein have the same meaning as commonly understood by a skill artisan in chemistry, biochemistry, cellular biology, molecular biology, and medical sciences.

The present inventors have surprisingly found that CMML patients display a higher proportion of a specific class of monocytes.

More specifically, the present inventors have found that the population of monocytes expressing CD14 but not CD16 (the so-called "classical" monocytes or CD14$^+$/CD16$^-$ monocytes) are hyper-represented in the blood of CMML patients. The proportion of this class of monocytes in the blood of CMML patients is much higher than in blood of healthy subjects or of patients affected with other blood diseases. As such, the proportion of classical monocytes is sufficient to discriminate between CMML and other blood diseases, such as e.g. MDS or MPN or reactive monocytosis. Therefore, the proportion of CD14$^+$/CD16$^-$ monocytes in the blood can be used as a positive diagnosis criterion for CMML.

The invention thus enables the skilled person to identify those subjects who are suffering from CMML by simply quantifying the CD14$^+$/CD16$^-$ monocytes in a blood sample from said subjects. Whereas the method of prior art relied on the identification of five criteria, four of which negative, a unique positive criterion is used in the method of the invention. This parameter can be determined in less than 24 hours, instead of the current 3 months. Thus the method of the invention is particularly advantageous because it generates a diagnosis in a very short time and with a very high degree of confidence, whereas the method currently recommended by WHO is both time-consuming and prone to mis-identification. In particular, the method of the invention shows both high sensitivity and high specificity.

In a first aspect, the present invention thus provides an in vitro method of diagnosis of chronic myelomonocytic leukemia (CMML) in a patient, said method comprising the steps of:

a) Detecting a monocyte population in a biological sample of said patient (for example by an exclusion gating strategy by cytometry), b) Quantifying the monocytes expressing high levels of CD14 but not expressing CD16 (CD14$^+$/CD16$^-$ monocytes) in said biological sample, c) Comparing the value of step b) to a reference value; and d) Diagnosing CMML based on said comparison.

A "subject" which may be subjected to the methodology described herein may be any of mammalian animals including human, dog, cat, cattle, goat, pig, swine, sheep and monkey.

More preferably, the subject of the invention is human subject; a human subject can be known as a patient. In one embodiment, "subject" or "subject in need" refers to a mammal, preferably a human, that suffers from CMML or is suspected of suffering from CMML or has been diagnosed with CMML. As used herein, a "CMML suffering subject" refers to a mammal, preferably a human, that suffers from CMML or has been diagnosed with CMML. A "control subject" refers to a mammal, preferably a human, which is not suffering from CMML, and is not suspected of being diagnosed with CMML.

As used herein, the term "biological sample" or "sample" refers to a whole organism or a subset of its tissues, cells or component parts. «Biological sample" further refers to a homogenate, lysate or extract prepared from a whole organism or a subset of its tissues, cells or component parts, or a fraction or portion thereof. The biological sample to be measured by the test method of the present invention is not particularly limited, as far as it can be collected from a mammal, preferably from a human; examples include humoral samples such as blood, bone marrow fluid, and lymph fluid, and solid samples such as lymph nodes, blood vessels, bone marrow, brain, spleen, and skin. Preferably, a "biological sample" according to the invention is any tissue which may contain monocytes, e.g., whole blood, plasma, or bone marrow.

Since monocytes are mostly found in the blood, it is particularly advantageous to use blood as a biological sample for the method of the invention. Indeed, such a blood sample may be obtained by a completely harmless blood collection from the subject and thus allows for a non-invasive diagnosis of CMML. The blood sample used in the method of the invention is preferably depleted of most, if not all erythrocytes, by common red blood cell lysis procedures. The detection is performed on the remaining blood cells, which are white blood cells (e.g., neutrophils, monocytes, lymphocytes, basophiles, etc.) and platelets.

Any volume used commonly by the person of skills in the art for hematological analyses will be convenient for the present method. For example, the volume of the blood sample can be of 100 µL, 200 µL, 300 µL, 400 µL, 500 µL, 600 µL, 700 µL, 800 µL, 900 µL, or 1000 µL.

Due to the label of granulocytes by CD16 antibody, it is essential to take in account the number of total granulocytes in the sample. When a blood sample presents a high number of granulocytes, the CD16 antibody is no longer saturating and the labeling of monocytes and granulocytes is not strong enough, and the distinction between CD16 positive cells and negative ones will be difficult to establish. To avoid this problem, when blood samples present more than 12×10$^9$/L of total granulocytes and preferably when blood samples present more than 10×10$^9$/L of total granulocytes, blood samples are preferably diluted to have a final concentration of total granulocytes under 10×10$^9$/L.

It is known in the art that morphological changes of blood cells begin after 30 minutes of drawing. Such changes consist in granulocyte swelling, increases of band forms, and or loss of specific granulation sometimes associated with vacuolization, especially in eosinophils and monocytes. It will be clear to the skilled person that the results of the method may be affected by the nature and the extent of the changes taking place. It is therefore preferable that the blood sample used in the method of the invention be fresh. By "a fresh blood sample", it is herein referred to a sample of blood which has been drawn within the previous 48 h, 24 h or 5 hours, preferably 4 hours, 3 hours, 2 hours, 1 hour, 30 minutes, or 15 minutes. Preferentially, the fresh blood sample of the invention will be kept at 4° C. until used.

As used herein, "diagnosis" or "identifying a subject having" refers to a process of determining if a subject is afflicted with a disease or ailment (e.g., CMML). More specifically, "diagnosing CMML" refers to the process of identifying if a subject suffering from a blood disorder suffers or not from CMML.

The first step of the method of the invention consists in detecting or purifying the monocyte population in the biological sample of the tested patient.

The term "monocytes" refers to a type of leukocytes (representing about 0.1 to 1×10$^9$/L of circulating leukocytes) produced by the bone marrow from hematopoietic stem cell precursors called monoblasts. They are produced in marrow, circulate briefly in blood, and migrate into tissues where they differentiate further to become macrophages.

Monocytes belong to the family of the peripheral mononuclear cell of the blood (PBMCs). PBMCs are a critical component in the immune system to fight infection and adapt to intruders. These cells can be extracted from whole blood using ficoll, a hydrophilic polysaccharide that separates layers of blood, which will separate the blood into a top layer of plasma, followed by a layer of PBMCs and a bottom fraction of polymorphonuclear cells (such as neutrophils and eosinophils) and erythrocytes.

Monocytes are fairly variable in size and appearance, but they show common expression of a number of markers. Three types of monocytes can be identified in human blood, based on the expression of the CD14 and CD16 markers: a) the "classical" monocyte or MO1 is characterized by high level expression of the CD14 cell surface receptor and no expression of CD16 (CD14$^+$/CD16$^-$ monocyte), b) the "non-classical" monocyte or MO3 shows low level or no expression of CD14 with additional co-expression of the CD16 receptor (CD14$^{low\ or\ -}$/CD16$^+$ monocyte), and c) the "intermediate" monocyte or MO2 with high level expression of CD14 and the same level of CD16 expression as the MO3 monocytes (CD14$^+$/CD16$^+$ monocytes) (Zawada et al., *Blood* 118(12):e50-61, 2011; Ziegler-Heitbrock et al., *Blood*, 116(16): e74-80, 2010; Wong et al., *Blood*, 118(5): e16-31, 2011).

Thus most of the monocytes, like classical monocytes, express the cluster of differentiation CD14. This cluster of differentiation has the sequence SEQ ID NO:1 in human (NP_000582.1). Numerous antibodies against human CD14 are commercially available. CD14 is expressed at the surface of the monocytic cells and, at 10 times lesser extent, of the neutrophils. Monocytes are easily identified by specific antigens (e.g., CD14 or CD16) combined with morphometric characteristics (e.g. size, shape, granulometry, etc.). For example, when flow cytometry is used, forward scatter and side scatter information help to identify the monocyte population among other blood cells.

In a particular embodiment, it is advantageous to analyze only the CD45 expressing-cells, in order to eliminate the contaminant blasts and to select mature cells, including all the monocytes. In this embodiment, the monocytes are detected in the CD45$^+$/SSC$^{intermediate}$ population of cell present in the biological sample. After exclusion of other contaminating populations, the CD14 and CD16 expression can be assessed.

Thus, in this preferred embodiment, the first step of the method of the invention comprises the detection and the measurement of CD45 expression at the cell surface and of the side scatter parameter (SSC) of the cells present in the biological sample.

The sequence of the cluster of differentiation CD45 is well-known. The CD45 molecules are single chain integral membrane proteins, comprising at least 5 isoforms, ranging from 180 to 220 kDa. They are generated by alternative splicing combinations of three exons (A, B, and C) of the genomic sequence. The non-restricted CD45 antigen, Leucocyte Common Antigen (LCA) consists of an extracellular sequence, proximal to the membrane, which is common to all CD45 isoforms. All the monoclonal antibodies that belong to the CD45 cluster react with this part of the antigen and are able to recognize all CD45 isoforms. These isoforms have extracytoplasmic sequences ranging from 391 to 552 amino acids long, with numerous N-linked carbohydrate attachment sites. The cytoplasmic portion contains two phospho-tyrosine-phosphatase domains.

Cells expressing CD45 at their surface are all human leucocytes (more precisely, lymphocytes, eosinophils, monocytes, basophils and neutrophils, with different level of expression). This cluster of differentiation is however absent from erythrocytes and platelets.

SEQ ID NO:7 represents the isoform 1 of the human CD45 (NP_002829.3) and SEQ ID NO:8 represents the isoform 2 of the human CD45 (NP_563578.2). The J33 monoclonal antibody binds to all the CD45 isoforms present on human leucocytes, in particular to isoforms 1 and 2 referred to in SEQ ID NO:7 and 8 respectively.

Expression of cell surface CD45 on monocytes may be assessed using specific antibodies, in particular using well known technologies such as cell membrane staining using biotinylation (or other equivalent techniques), followed by immunoprecipitation with specific antibodies, flow cytometry, western blot, ELISA or ELISPOT, antibodies microarrays, or tissue microarrays coupled to immunohistochemistry.

Preferably, the expression of cell surface CD45 is detected by flow cytometry. Flow cytometry is a useful tool for simultaneously measuring multiple physical properties of individual particles (such as cells). Cells pass single-file through a laser beam. As each cell passes through the laser beam, the cytometer records how the cell or particle scatters incident laser light and emits fluorescence. Using a flow cytometric analysis protocol, one can perform a simultaneous analysis of surface molecules at the single-cell level.

In this embodiment, the use of fluorochromic agents attached to anti-CD45 antibodies to enable the flow cytometer to sort on the basis of size, granularity and fluorescent light is highly advantageous. Thus, the flow cytometer can be configured to provide information about the relative size (forward scatter or "FSC"), granularity or internal complexity (side scatter or "SSC"), and relative fluorescent intensity of the cell sample. The fluorescent light sorts on the basis of CD45-expressing, enabling the cytometer to identify and enrich for these monocytes.

It is possible to use all the anti-CD45, anti-CD14 and anti-CD16 antibodies at the same time, provided that these antibodies are labelled with fluorophores emitting in distinguishable wavelengths. This strategy enables the identification of all types of cells with respect to CD45, CD14 and CD16: those expressing CD45 and CD14 and not CD16 (MO1), those expressing CD45 and CD14 and CD16 (MO2 or a part of MO3), and those expressing CD45 and CD16 but not CD14 (most of the MO3).

In a preferred embodiment, the step a) of the invention requires to detect a substantially pure monocyte population, that is, a population of monocytes that is devoid of contaminant cells. As used herein, "contaminant cells" or "contaminant white blood cells" refer to the white blood cells which are present in the blood sample of the subject and which are not monocytes. Such contaminant cells include granulocytes, e.g. neutrophils, eosinophils, basophils, and lymphocytes, e.g., T cells, NK cells, B cells, but also precursors of these cell types.

"Granulocytes" are a type of leukocytes characterized by the presence of granules in their cytoplasm. The types of these cells are neutrophils, eosinophils, and basophils.

"T cells" or "T lymphocytes" are a type of lymphocyte that plays a central role in cell-mediated immunity. They can be distinguished from other lymphocytes, such as B cells and natural killer cells (NK cells), by the presence of a T-cell receptor (TCR) on the cell surface.

"B cells" or "B lymphocytes" are a type of lymphocyte in the humoral immunity of the adaptive immune system. They can be distinguished from other lymphocytes, such as T cells and natural killer cells (NK cells), by the presence of a protein on the B cells outer cell surface known as a B-cell receptor (BCR).

"Natural killer cells" (or "NK cells") are a type of cytotoxic lymphocytes that kill cells by releasing small cytoplasmic granules of proteins called perforin and granzyme. They constitute the third kind of cells differentiated from the common lymphoid progenitor generating B and T lymphocytes.

The remaining white blood cells are identified and counter-selected on the basis of the expression of specific markers.

The existence of markers which are specific for each of the contaminant cell types enables the identification of these cells in the blood sample of the subject. Identified contaminant cells can then be removed from the sample (i.e., physically) or from the analysis (i.e., by retaining only the data pertaining to the monocyte population for the analysis), so that the study then only focuses on the monocyte population. In this respect, although any of the above-mentioned analytical techniques can be used to identify the said contaminant white blood cells, flow cytometry is particularly adapted for this task, since it enables the skilled person to eliminate the contaminants and analyze the monocyte population with minimal effort.

In this respect, any antibodies directed against one or more antigens expressed by one or more of the contaminant cells can be used to identify the said contaminant white blood cells. In a particular embodiment, antibodies specific for well-known antigens expressed by granulocytes (CD24, CD15, CD16), T lymphocytes (CD2, CD3), B lymphocytes (CD24, CD19), and/or NK cells (CD2 and/or CD56) can be used in step a).

Using anti-CD15, anti-CD16, anti-CD56, anti-CD2 or anti-CD24 antibodies therefore enables to detect and therefore exclude the cells expressing CD2, CD56 and CD24 proteins, notably the $CD2^+$ T lymphocytes, the $CD2^+$ NK cells, the $CD56^+$ NK cells, the $CD24^+$ immature granulocytes as well as the $CD15^+$ or $CD16^{++}$ granulocytes.

In a preferred embodiment, the antibodies used to identify and/or to remove the contaminant cells according to the method of the invention comprise anti-CD16, anti-CD56, anti-CD2, and anti-CD24 antibodies. Of note, anti-CD15 antibodies may be used instead of anti-CD16 antibodies in order to detect the granulocytes.

According to the present invention, a cell "expresses CD56" (or CD15 or CD16 or CD2 or CD24) if CD56 (or CD15 or CD16 or CD2 or CD24) is present at a significant level on its surface (such a cell being also defined as a "$CD56^+$ cell", or a "$CD15^+$ cell", a "$CD16^+$ cell", a "$CD2^+$ cell" or a "$CD24^+$ cell", respectively). In particular, a cell expresses CD56 (or CD15 or CD16 or CD2 or CD24) if the signal associated to surface CD56 (or CD15 or CD16 or CD2 or CD24) staining (e.g. obtained with an antibody anti-CD56 coupled to a fluorescent marker) which is measured for said cell is superior to the signal corresponding to the staining of one cell being known as not expressing CD56 (or CD15 or CD16 or CD2 or CD24).

In a preferred embodiment, $CD56^+$ cells ($CD15^+$ cells, $CD16^+$ cells, $CD2^+$ cells or $CD24^+$ cells) are such that the ratio between the surface $CD56^-$ (or $CD15^-$ or $CD16^-$ or $CD2^-$ or $CD24^-$) associated signal measured for said cells and the surface $CD56^-$ (or $CD15^-$ or $CD16^-$ or $CD2^-$ or $CD24^-$)-associated signal measured for cells being known as expressing CD56 (or CD15 or CD16 or CD2 or CD24) is positive (i.e., above 0). Cells expressing CD56 (or CD2 or CD24) at their surface are well known in the art. Cells expressing CD56 include NK cells, while cells expressing CD2 are, for example, T lymphocytes and cells expressing CD24 are for example B lymphocytes. Cells that do not express CD56 are for example B lymphocyte.

The sequences of the clusters of differentiation CD56, CD2 and CD24 are well known in the art, and can be retrieved under the accession numbers NP_000606, NP_001758, and NP_037362, respectively. The sequences of these proteins are represented by the sequences of SEQ ID NO: 4-6 respectively.

The cluster of differentiation CD15 is the fucosyltransferase 4 (alpha (1,3) fucosyl transferase). In human, it has the sequence SEQ ID NO:9 (NP_002024). Cells expressing CD15 are for example granulocytes.

CD16, the low affinity receptor for the Fc part of IgG (therefore also known as FcγRIII), is a glycoprotein expressed in monocytes, and also in NK cells and neutrophils. Two isoforms (A and B) exist. In human, the isoform A has the sequence SEQ ID NO:2 (NP_000560.5) and the isoform B has the sequence SEQ ID NO:3 (NP_001231682.1).

Several monoclonal antibodies have been produced against the isoforms A and B of CD16/FcγRIII and the corresponding epitopes have been localized on these proteins (see e.g. Fleit et al., *Clin Immunol Immunopathol.*, 59(2): 222-235, 1991; Fleit et al., *Clin Immunol Immunopathol.*, 62(1 Pt 1): 16-24, 1992; Tamm A. et al., *J Immunol.*, 157(4): 1576-1581, 1996). Antibodies against CD16 are available commercially.

As used herein, a cell "expresses CD16" if CD16 is present at a level on its surface (such a cell being also defined as a "$CD16^+$ cell"). In particular, a cell expresses CD16 if the signal associated to surface CD16 staining (e.g. obtained with an antibody against CD16 coupled to a fluorescent marker) which is measured for said cell is higher than the signal corresponding to the same staining of at least one cell being known as no expressing CD16, such as B lymphocytes. In other terms, the ratio between the surface CD16-associated signal measured for said cell and the surface CD16-associated signal measured for at least one cell being known as not expressing CD16 (e.g., a B lymphocyte) is positive (i.e., superior to 0).

In a preferred embodiment of the invention, step a) comprises the steps of:
- Excluding the $CD2^+$ cells from the analysis (in order to eliminate the contaminant T lymphocytes and a part of the NK cells);
- Excluding the $CD56^+$ cells from the analysis (in order to eliminate the remaining contaminant NK cells);
- Excluding the $CD16^{++}$ or the $CD15^+$ cells from the analysis (in order to eliminate the granulocyte cells); and/or
- Excluding the $CD24^+$ cells from the analysis (said cells corresponding to granulocytes and B lymphocytes).

In a preferred embodiment, the antibodies used to identify and/or to remove the contaminant cells according to the method of the invention are chosen in the group consisting of: anti-CD15, anti-CD16, anti-CD56, anti-CD2, anti-CD24, and anti-CD16 antibodies.

The monocytes to be detected in step a) of the method of the invention are therefore preferably the CD45+, $CD14^+$, $CD15^-$, $CD16^-$, $CD2^-$, $CD56^-$, and/or $CD24^-$ cells present in the biological sample of the subject.

Expression of these cell surface antigens may be notably assessed using well known technologies such as cell membrane staining using biotinylation or other equivalent techniques followed by immunoprecipitation with specific antibodies, flow cytometry, western blot, ELISA or ELISPOT, antibodies microarrays, or tissue microarrays coupled to immunohistochemistry. Other suitable techniques include FRET or BRET, single cell microscopic or histochemistry methods using single or multiple excitation wavelength and applying any of the adapted optical methods, such as electrochemical methods (voltametry and amperometry techniques), atomic force microscopy, and radio frequency methods, e.g. multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry), cell ELISA, radioisotopic, magnetic resonance imaging, analysis by polyacrylamide gel electrophoresis (SDS-PAGE); HPLC-Mass Spectroscopy; Liquid Chromatography/Mass Spectrometry/Mass Spectrometry (LC-MS/MS)).

In a preferred embodiment, the detection of these cell surface antigens is performed by an exclusion gating strategy by flow cytometry. Flow cytometry is a powerful technology that allows researchers and clinicians to perform complex cellular analysis quickly and efficiently by analyzing several parameters simultaneously. The amount of information obtained from a single sample can be further expanded by using multiple fluorescent reagents. The information gathered by the flow cytometer can be displayed as any combination of parameters chosen by the skilled person.

According to this embodiment, each of the antibodies (e.g., anti-CD15, anti-CD56, anti-CD2, anti-CD24, and/or anti-CD16 antibodies) is labelled with a specific fluorochrome, enabling the cytometer to identify the contaminant cells carrying the antigen recognized by said antibody, and thus the selection of the cells which do not carry the antigen. The fluorochromes which can be used in this embodiment are well known in the art. They include such fluorochromes as e.g., PE, APC, PE-Cy5, Alexa Fluor 647, PE-Cy-7, PerCP-Cy5.5, Alexa Fluor 488, Pacific Blue, FITC, AmCyan, APC-Cy7, PerCP, and APC-H7.

The identification of the various contaminant cells by flow cytometry can be performed sequentially or simultaneously. Preferably, the identification of the various contaminant cells in the sample is performed simultaneously.

According to a specific embodiment, the cells present in the biological sample of the patient are contacted with antibodies, each of which recognizing a specific antigen expressed by the monocytes or by one or more of the contaminant cells (e.g., CD45, CD15, CD56, CD2, CD24, and/or CD16), and each of which being labelled with a specific fluorochrome. The sample is then analyzed by flow cytometry.

The diagnosis methods of the invention can be practiced with any antibody or antiserum detecting (or recognizing specifically) the antigens expressed by the monocytes or by the contaminating cells.

The present inventors have surprisingly found that the proportion of classical monocytes ($CD14^+/CD16^-$ monocytes, or MO1) is sufficient to discriminate between CMML and other blood diseases, such as e.g. MDS or MPN or reactive monocytosis. They therefore propose to use the proportion of $CD14^+/CD16^-$ monocytes in the blood as a positive diagnosis criterion for CMML.

According to the method of the invention, the absolute, raw numbers of $CD14^+/CD16^-$ monocytes present in the biological sample of the subject may be used to determine if said subject has CMML. However, it is advantageous to normalize this value to the total population of monocytes in the said sample.

Accordingly, a preferred embodiment relates to a method for diagnosing CMML in a subject, wherein step b) further comprises the steps of quantifying all the monocytes (that is, calculating the number or the concentration of cells of the MO1, MO2 and MO3 populations) in said biological sample and calculating the ratio of $CD14^+/CD16^-$ monocytes (MO1) to all monocytes. This ratio is then compared to a reference value to determine if the said subject suffers from CMML.

In another preferred embodiment, step b) of said method further comprises the steps of quantifying the MO3 monocytes in said biological sample and calculating the ratio of $CD14^+/CD16^-$ monocytes (MO1) to the MO3 monocytes. This ratio is then compared to a reference value to determine if the said subject suffers from CMML.

The term "reference value", as used herein, refers to the expression level of a CMML diagnosis marker under consideration (e.g., $CD14^+/CD16^-$ monocytes) in a reference sample. A "reference sample", as used herein, means a sample obtained from subjects, preferably two or more subjects, known to be suffering from CMML. The suitable reference expression levels of CMML diagnosis marker can be determined by measuring the expression levels of said CMML diagnosis marker in several suitable subjects, and such reference levels can be adjusted to specific subject populations. The reference value or reference level can be an absolute value; a relative value; a value that has an upper or a lower limit; a range of values; an average value; a median value, a mean value, or a value as compared to a particular control or baseline value. A reference value can be based on an individual sample value such as, for example, a value obtained from a sample from the subject being tested, but at an earlier point in time. The reference value can be based on a large number of samples, such as from population of subjects of the chronological age matched group, or based on a pool of samples including or excluding the sample to be tested.

In this regard, the present inventors have shown that it is particularly advantageous to use a threshold value of 93.6% for the proportion of classical monocytes MO1 in the total monocyte population. The ratio of classical (MO1) to total monocytes or to MO3 monocytes in healthy subject, as well as in subjects suffering from other blood disorders, is well below this threshold. Hence, this value ensures that the method of the invention gives a diagnosis with both high sensitivity and high specificity. As used herein, sensitivity=TP/(TP+FN); specificity is TN/(TN+FP), where TP=true positives; TN=true negatives; FP=false positives; and FN=false negative. Clinical sensitivity measures how well a test detects patients with the disease (e.g., CMML); clinical specificity measures how well a test correctly identifies those patients who do not have the disease (e.g., CMML). It is obviously also possible to detect the percentage of MO2 and MO3 monocytes in the total population of monocytes and to compare this value to the threshold of 6.4%. Patients having less than 6.4% of monocytes MO2 and MO3 should have more than 93.6% of monocytes MO1 and are therefore likely to suffer from CMML. Detecting the MO2+MO3 monocyte numbers is therefore a way to reduce to practice the method of the invention.

Thus in a preferred embodiment, the reference value of the method is 93.6%. More preferably, the said reference value is 93.7%, 93.8%, 93.9%, 94%, 94.5%, 95%, 95.5%, 96%, 96.5%, 97%, 97.5%, 98%, 98.5%, 99%, or 99.5%. In other words, a subject has CMML if the ratio of $CD14^+/CD16^-$ monocytes to all the monocytes or to MO3 monocytes of said subject is higher than 0.936, preferably higher than 0.937, 0.938, 0.939, 0.94, 0.945, 0.95, 0.955, 0.96, 0.965, 0.97, 0.975, 0.98, 0.985, 0.99, or 0.995.

In the context of the present invention, a cell "expresses CD14" if CD14 is present at a significant level at its surface (such a cell being also defined as a "$CD14^+$ cell"). In particular, a cell expresses CD14 if the signal associated to surface CD14 staining (e.g., obtained with an antibody anti-CD14 coupled to a fluorescent marker) which is measured for said cell is similar or identical to the signal corresponding to the same staining of at least one cell being known as expressing CD14.

In a preferred embodiment, CD14$^+$ cells are such that the ratio between the surface CD14-associated signal measured for these cells and the surface CD14-associated signal measured for cells being known as not expressing CD14 is positive (i.e., superior to 0). Cells expressing CD14 at their surface are well known in the art. They are for example classical and intermediate monocytes. Cells that do not express CD14 are for example T lymphocytes.

In the context of the present invention, a cell "expresses CD16" if CD16 is present at a significant level at its surface (such a cell being also defined as a "CD16$^+$ cell"). Assessment of CD16 expression can be performed as mentioned previously for CD14$^+$ cells. Cells expressing CD16 at their surface are well known in the art. They are for example monocytes, NK cells, and neutrophils.

On another hand, a cell is said to be "CD16$^-$" or "CD16$^{low}$" if the signal associated to surface CD16 staining (e.g., obtained with an antibody anti-CD16 coupled to a fluorescent marker) which is measured for said cell is similar or identical to the signal corresponding to the same staining of at least one cell being known as not expressing CD16.

In a preferred embodiment, CD16$^-$ cells are such that the ratio between the surface CD16-associated signal measured for these cells and the surface CD16-associated signal measured for at least one cell being known as not expressing CD16 is of about 1. Preferably, the surface CD16-associated signal of the target cells is compared to an average surface CD16-associated signal measured on a population of cells being known as not expressing CD16, so that the ratio between the surface CD16-associated signal measured for the target cells and the average surface CD16-associated signal measured on a population of cells being known as not expressing CD16 is of about 1. Cells that do not express CD16 at their surface are well known in the art. They are for example B lymphocytes.

The quantification of CD14$^+$/CD16$^-$ monocytes thus preferably involves contacting the patient's biological sample with an anti-CD14 antibody and an anti-CD16 antibody so as to determinate the level of surface CD14 and CD16 expression.

The term "antibody" as used herein is intended to include monoclonal antibodies, polyclonal antibodies, and chimeric antibodies. Antibody fragments can also be used in the present diagnosis method. This term is intended to include Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

The antibodies used in the method of the invention can be of different isotypes (namely IgA, IgD, IgE, IgG or IgM).

They may be from recombinant sources and/or produced in transgenic animals. Conventional techniques of molecular biology, microbiology and recombinant DNA techniques are within the skill of the art. Such techniques are explained fully in the literature.

Commercial antibodies recognizing specifically the antigens expressed by blood cells can be furthermore used. Some of them are listed in the experimental part below (said list being however not exhaustive nor limiting).

These antibodies can be detected by direct labeling with detectable markers. Alternatively, unlabeled primary antibody can be used in conjunction with a labeled secondary antibody, comprising antisera, polyclonal antisera or a monoclonal antibody specific for the primary antibody. Immunohistochemistry protocols and kits are well known in the art and are commercially available.

In a preferred embodiment of the invention, these antibodies are tagged with a detectable marker, preferably a fluorescent or a luminescent marker. Examples of detectable markers/labels include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase examples of suitable prosthetic group complexes include streptavidin/biotin and avidin/biotin, examples of suitable fluorescent materials include umbelliferone, fluorescein, fluorescein isothiocyanate, rhodamine, dichlorot[pi]azinylamine fluorescein, dansyl chloride or phycoerythrin, an example of a luminescent material includes luminol, examples of bioluminescent materials include luciferase, luciferin, and aequorin, and examples of suitable radioactive material include $^{125}$I, $^{131}$I, $^{35}$S or $^3$H.

The present diagnostic tool may also assist physicians in identifying patients who are likely to progress towards even more serious form of CMML and thus may suggest those patients require heavier or more aggressive treatment.

As used herein, the terms "treat", "treating", "treatment", and the like refer to reducing or ameliorating the symptoms of a disorder (e.g., CMML, and/or symptoms associated therewith. It will be appreciated that, although not precluded, treating a disorder or condition does not require that the disorder, condition or symptoms associated therewith be completely eliminated.

As used herein "treating" a disease in a subject or "treating" a subject having a disease refers to subjecting the subject to a pharmaceutical treatment, e.g., the administration of a drug, such that the extent of the disease is decreased or prevented. For examples, treating results in the reduction of at least one sign or symptom of the disease or condition. Treatment includes (but is not limited to) administration of a composition, such as a pharmaceutical composition, and may be performed either prophylactically, or subsequent or the initiation of a pathologic event. Treatment can require administration of an agent and/or treatment more than once.

The invention thus also relates to in vitro methods for selecting a therapy for a patient with CMML comprising the steps of:

a) Detecting the monocyte population in a sample from the patient (for example by an exclusion gating strategy by flow cytometry, as described above), b) Quantifying the CD14$^+$/CD16$^-$ monocytes in a sample from the patient, e.g., by one of the methods described above, and c) Selecting a CMML therapy based on the level of the CD14$^+$/CD16$^-$ monocytes.

In one embodiment, the patient is selected for a treatment with a CMML therapy (e.g., a DNA methyltransferase inhibitor) if the CD14$^+$/CD16$^-$ monocytes are present in the sample at a high level. In some embodiments, the patient is treated for CMML using therapeutically effective amount of the CMML therapy. Thus, in some embodiments, the patient is selected for a treatment with a CMML therapy (e.g., a DNA methyltransferase inhibitor) if the patient's sample displays CD14+/CD16− monocytes at a high level, and (following the selection) the patient is treated for CMML using therapeutically effective amount of the CMML therapy.

Therapies for CMML include various chemotherapeutic regiments such as e.g., topotecan, hydroxyurea, anthracyclines-Ara C, cytarabine, bortezomib, farnesyl tranferase inhibitors, histone deacetylase inhibitors, arsenic trioxide, and DNA methyltransferase inhibitors, such as 5-azacitidine, 5-aza-2'-deoxyazacytidine, or decitabine. Preferably, a therapy for CMML is a DNA methyltransferase inhibitor. More preferably, said inhibitor is decitabine.

The invention also relates to an in vitro method for assessing the efficacy of a therapy in a patient suffering from a CMML, said method comprising the steps of:
 a) Quantifying the CD14+/CD16− monocytes in a sample obtained from said subject during or after said treatment,
 b) Quantifying the CD14+/CD16− monocytes in a sample obtained from said subject before said treatment, and
 c) Assessing the efficacy of therapy based on the comparison of the value of step a) with a value of step b).

The invention is also drawn to an in vitro method of adapting the CMML therapy of a CMML-suffering subject, comprising:
 a) Assessing the efficacy of said therapy as described above, and
 b) Adapting the therapy based on the result of step a).

According to a preferred embodiment, a decreased level of the CD14+/CD16− monocytes after treatment compared to the level determined before treatment is indicative of the efficiency of the CMML therapy for said subject. On the other hand, a level of the CD14+/CD16− monocytes which is unchanged or even increased after the treatment is indicative of a treatment which is inefficient. In this case, it may be necessary to select a more aggressive therapy or even to consider a bone marrow transplantation or stem cell transplantation.

Thus, said adaptation of the CMML therapy may consist in:
 the continuation, a reduction or suppression of the said CMML therapy if the therapy has been assessed as efficient, or
 an augmentation of the said CMML therapy or a change to a more aggressive therapy, if said therapy of step a) has been assessed as non-efficient.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Having generally described this invention, a further understanding of characteristics and advantages of the invention can be obtained by reference to certain specific examples and figures which are provided herein for purposes of illustration only and are not intended to be limiting unless otherwise specified.

EXAMPLES

Material and Methods

Samples Selection

Three French university hospital laboratories participated in this study.

Settings of the Flow Cytometers

A setting harmonization between the three different center instruments was realized. The optimal PMT voltage for each fluorescence channel was first determined using the Navios of one center (HM). Using these voltage settings, Versacomp beads (Beckman Coulter) labeled with each antibody were run on the Navios, without compensation. The median fluorescence intensity of the positive peak was recorded for each of the eight fluorescence channels. Then these target values were used as the median fluorescence intensity target values for setting up PMT voltages on the two other Navios instruments. Thereafter, each center calculated its own spectral compensation matrix.

Instruments setting were checked daily using Flow-Check Pro and Flow-Set Pro beads (Beckman Coulter) as recommended by the manufacturer.

Patient Peripheral Blood Samples

Blood samples of the learning cohort were prospectively collected on ethylenediaminetetraacetic acid (EDTA) from patients with CMML diagnosis according to the WHO 2008 classification (n=43), age-matched healthy donors (n=26), patients with another hematopoietic malignancy (n=16), and patients with reactive monocytosis (n=32). These samples were collected after informed consent according to the Declaration of Helsinki. The learning cohort also including monocytes sorted from blood donor buffy coats (n=23).

The validation cohort included 186 blood samples collected from CMML patients (n=28), patients with a myelodysplastic syndrome (MDS; n=28), patients with a reactive monocytosis (n=63) and age-matched healthy donors (n=67).

Other hemopathies are composed of: 5 lymphoid hemopathies (3 monoclonal gammapathy, 1 lymphocytose LGL, 1 LLC) 1 bicytopenia 3 hyperleucocytoses, 1 AREB, 1 JMML, 1 atypical MPN, 2 Vaquez, 4 myelofibrosis, 2 TE.

CMML diagnosis and stratification, counting promonocytes as blasts, were based on WHO 2008 criteria (Vardiman et al., *Blood* 114:937-951, 2009). Peripheral IMC (immature myeloid cells) represent the sum of peripheral blood blasts, promyelocytes, myelocytes, and metamyelocytes, according to MDAPS (MD Anderson Prognostic Scoring System) (Onida et al., *Blood* 99:840-849, 2002).

Multi-Fluorochrome Staining of Learning Cohort Samples

Roughly three millions of peripheral blood mononuclear cells (PBMC) were sorted from peripheral blood samples by Ficoll Hypaque, washed with ice-cold phosphate buffered saline (PBS), and incubated at 4° C. for 30 minutes with human Trustain FcX (Biolegend) as recommended by the manufacturer. PBMC were then labeled with anti-CD45, -CD24, -CD14, -CD16, -CD115, -CD62L, -CD64, -CCR2 and -CX3CR1 antibodies (BD Biosciences, table 1) and analyzed by flow cytometry using a LSRII (BD Biosciences). Acquisition was stopped after collection of 50,000 events in monocyte gate (defined in FIG. 1).

TABLE 1

Human Antibodies used for the phenotyping of PBMC

| Antigen | Antibody name | Clone (Isotype) | Fluorochrome | Company | Reference |
|---|---|---|---|---|---|
| Human monocytes, PBMC | | | | | |
| CX3CR1 | Rat Anti-Human CX3CR1 | 2A9-1 (IgG2b) | FITC | Biolegend | 341606 |
| CCR2 | Mouse Anti-Human CD192 | TG5/CCR2 (IgG2b, K) | PerCP-CY5.5 | Biolegend | 335303 |
| CD62L | Mouse Anti-Human CD62L | DREG-56 (IgG1, K) | PE-CY7 | Biolegend | 304822 |
| CD45 | Mouse Anti-Human CD45 | J.33 (IgG1) | Krome orange | Beckman Coulter | A96416 |
| CD24 | Mouse Anti-Human CD24 | ALB9 (IgG1) | R-PE, texas Red | Beckman Coulter | B12699 |
| CXCR1 | Mouse Anti-Human CD181 | 8F1/CXCR1 (IgG2b) | APC | Biolegend | 320612 |
| CD14 | Mouse Anti-Human CD14 | M5E2 (IgG2a) | Pacific blue | Becton Dickinson | 558121 |
| CD16 | Mouse Anti-Human CD16 | 3G8 (IgG1) | APC-CY7 | Becton Dickinson | 560195 |
| CD64 | Mouse Anti-Human CD64 | 10.1 (IgG1) | Alexa fluor 700 | Becton Dickinson | 561188 |
| CSF-1R | Rat Anti-Human CD115 | 9-4D2-1E4 (IgG1, K) | PE | Biolegend | 347304 |
| Human monocytes, whole blood | | | | | |
| CD45 | Mouse Anti-Human CD45 | J.33 (IgG1) | Krome orange | Beckman Coulter | A96416 |
| CD24 | Mouse Anti-Human CD24 | ALB9 (IgG1) | PE | Beckman Coulter | IM1428U |
| CD2 | Rat Anti-Human CD2 | 39C1.5 (IgG2a) | APC | Beckman Coulter | A60794 |
| CD14 | Mouse Anti-Human CD14 | RMO52 (IgG2a) | PE-CY7 | Beckman Coulter | A22331 |
| CD16 | Mouse Anti-Human CD16 | 3G8 (IgG1) | Pacific Blue | Beckman Coulter | A82792 |
| CD56 | Mouse Anti-Human CD56 | N901 (IgG1) | PC5.5 | Beckman Coulter | A79388 |
| CD64 | Mouse Anti-Human CD64 | 22 (IgG1) | FITC | Beckman Coulter | IM1604U |

Table 1 shows the characteristics of each antibody that was used to perform this protocol, including antigen, antibody name, conjugated fluorochrome, catalog number and information about the provider company.

The FIG. 1 discloses the gating strategy for human monocyte subsets analysis in PBMC by flow cytometry. This analysis was based on an ongoing exclusion gating strategy. Labeled leukocytes were acquired using a LSRII Flow cytometer and analyzed with Kaluza software. (A) Monocytes were first roughly selected on morphological parameters (FSC versus SSC) including a part of lymphocytes and polymorphonuclears (PMN). Doublets were excluded using a FSC-int vs FSC peak (data not shown). (B) Monocytes were defined as CD45$^+$/SSC intermediate cells. (C) Granulocytes and B cells were both selected as CD24$^+$ cells. (D) CD16$^{high}$ granulocytes (PMN) and NK cells were next isolated. (E) After exclusion of the contaminating populations of panels C and D, the remaining population was then subjected to the criteria CD16 and CD14 and the double negative population was depleted. (F) The remaining population was divided on the CD14 and CD16 expression between CD14$^+$ CD16$^-$ (classical), CD14$^+$ CD16$^+$ (intermediate) and CD14$^{low}$ CD16$^+$ (non classical) monocytes.

Multi-Fluorochrome Staining of Validation Cohort Samples

Briefly, 200 μL of whole peripheral blood have been labeled with anti-CD45, -CD24, -CD2, -CD14, -CD16 and -CD56 (Beckman Coulter, table 1) according to the manufacturer recommendations. After 30 minutes of incubation in the dark, red blood cells were lysed and fixed with 1 mL of Versalyse and 25 μL of iotest (Beckman Coulter). Samples were analyzed within 24 h of collection by flow cytometry (Navios, Beckman Coulter). Acquisition was stopped after collection of 40,000 events in the CD14$^+$, CD16-(MO1) monocyte gate (defined in FIG. 2). Centers provided flow cytometry standard listmode data (FCS) for each sample generated on-site.

The FIG. 2 discloses an overview of the exclusion gating strategy for human monocyte subsets analysis in total blood cells by flow cytometry.

Six color-labeled leukocytes were acquired using CXP-Navios software with a Navios Flow cytometer and analyzed with Kaluza software. Sequence of dot-plots shows the gating strategy used to identify the monocytes subpopulations. (A) Monocytes were first roughly selected on morphological parameters (FSC versus SSC) including a part of lymphocytes and polymorphonuclears (PMN). Doublets were excluded using a FSC-int vs FSC peak (data not shown). (B) On the remaining population selected (singulets gate), CD2$^+$ T cells were first selected. (C) Then, NK cells were defined as CD56$^+$ cells. (D) Isolated CD16$^{high}$ granulocytes (PMN) are isolated. (E) Finally, B cells and immature granulocytes were both selected as CD24$^+$ cells. (F) Platelets clumps, cell debris and red blood cells were excluded as CD45$^{low}$ events. These populations were considered as contaminating populations. A monocyte population was then defined on CD45 vs SSC dot-plot as CD45$^+$/SSC intermediate. (G) After exclusion of the contaminating populations of panels B, C, D and E, the remaining population was then subjected to the criteria CD16 and CD14 and the double negative population was depleted. (H) Finally, from the remaining population, defined as pure monocyte populations, were identified the three monocytes subsets.

In order to have enough cells to analyze in appropriate concentration, we labelled 200 µL of whole blood but used only 1 mL of versalyse.

Also, we diluted the blood samples when leucocyte concentration was more than 10 G/L (because of CD16 titration by granulocytes).

Flow Cytometry Analysis of Monocytes Subsets

The FCS files obtained from both learning and validation cohorts were analyzed centrally (DSB) in a blind fashion using Kaluza software (Beckman Coulter). The analysis was based on an exclusion gating strategy (as detailed in FIGS. 1 and 2). First, monocytes were gated on a CD45 versus side-angle scatter (SSC) dot plot as $CD45^{high}$/SSC intermediate cells. To exclude contaminating cells in the monocyte population when analyzing PBMCs, we defined a NK-$CD16^{pos}$ gate, a PMN-$CD16^{pos}$ gate and a $CD24^{pos}$ gate, to exclude NK cells, remaining granulocytes, and B lymphocytes & immature granulocytes, respectively (cf. FIG. 1). To exclude contaminating cells in the monocyte population when analyzing whole blood samples, we defined a LT-$CD2^{pos}$ gate, a NK-$CD56^{pos}$ gate, a PMN-$CD16^{pos}$ gate and a $CD24^{pos}$ gate to exclude T lymphocytes, NK cells, granulocytes, and B lymphocytes & immature granulocytes, respectively (cf. FIG. 2). These contaminating gates were excluded using Boolean equation.

It is better to analyze the CD2 and CD56 markers versus SSC in order to avoid the depletion of monocytes that can be positive for these markers (Lacronique-Gazaille et al, Haematologica 92(6):859-860, 2007).

Moreover, it is advantageous to use the CD24 marker in order to avoid contamination by immature granulocytes, which can be found in some CMML samples (Droin et al., Blood 115(1):78-88, 2010).

On the remaining cells, three monocyte subsets were identified according to their relative expression of CD14 and CD16: $CD14^+$/$CD16^-$ or classical monocytes (MO1), $CD14^+$/$CD16^+$ or intermediate monocytes (MO2), and $CD14^{low}$/$CD16^+$ or non-classical monocytes (MO3) (Wong et al., Blood, 118(5): e16-31, 2011).

Expression of some monocyte markers such as CD14 and CD64 is restricted to monocyte subsets, mainly MO1 and MO2. A positive selection, based on the expression of one of these markers, leads to misgating the $CD14^{low}$/$CD64^{low}$ MO3 subset.

It is better to collect at least 40,000 events in the MO1 gate to ensure an accurate estimation of the monocyte subset repartition.

Percentage of Classical Monocytes Cut-Off

The cut-off of classical monocyte percentages was obtained from a Receiver Operating Characteristics (ROC) curve using MedCalc software. MO1 percentages of both CMML patient and "not CMML patients" (young and age-matched controls, others hemopathies and reactive monocytosis) were used.

Results

Quantification of Monocytes Subsets in CMML

First, we focused on the biology of human monocyte subsets from peripheral blood mononuclear cells (PBMC) by flow cytometry. Using an exclusion strategy to deplete the contaminating populations (described in FIG. 1), we identified monocytes as a $CD45^+$/SSC intermediate population. Within this population, MO1 ($CD14^+$/$CD16^-$), MO2 ($CD14^+$/CD16+) and MO3 ($CD14^{low}$/CD16+) were identified as previously described (Wong et al., Blood, 118(5): e16-31, 2011). Each of these three latter populations was cell-sorted and analyzed by morphology after May-Grün-wald-Giemsa (MGG) staining to assure the monocyte purity after these gating strategies (cf. FIG. 3A). Moreover, these three monocytes subsets were identified by distinct expression profiles of trafficking (CCR2, CX3CR1) and myeloid function or differentiation (CD64, CD62L, CD115, CD181) markers as well at protein membrane level (cf. FIG. 3B) and at mRNA level (cf. FIG. 3C).

We assessed the level of MO1 population in a learning cohort of 140 patients. Similar monocyte subset profiles were obtained from 49 young or aged-control donors, consisting of 86.3±0.9% (SEM) MO1 for healthy young donors (n=23) and 82.7±1.4% MO1 for aged-controls (n=26) (cf. FIG. 4A, 4B and FIG. 5A). Compare to controls, the monocyte subset profiles of 43 CMML patients were utterly different with a strong increase in MO1 percentage: 96.75±1.6% of MO1 population and a nearly total absence of MO2 and MO3 populations (cf. FIG. 4C and FIG. 5A). All other hemopathies showed a normal repartition of monocyte subsets with 83.9±2% of MO1 population (n=16) and 78.9±1.88% of MO1 in reactive monocytosis (n=30, p<0.001) (cf. FIG. 4D and FIG. 5A). The Krushall-Wallis test showed a significant difference in the distribution of MO1 level across the group (controls, other hemopathies or reactive monocytosis) and CMML samples but no difference across the distinct group of not CMML samples.

The MO1 percentage for CMML patients was observed to be independent of the absolute number of circulating monocytes, the gene mutation pattern, the proliferative versus dysplastic status of the disease according to the FAB criteria (leukocyte count cut-off value $13.10^9$/L), and the disease subtype (type 1 versus type 2) according to WHO criteria (not shown).

Our data show that a specific phenotypic signature of monocyte subsets can be found in CMML peripheral blood.

Percentage of Classical Monocyte Subset as a Specific and Sensitive Tool for CMML Diagnostic To determine if quantitative analysis of MO1 percentage in PBMC could distinguish CMML samples from other ones, a ROC curve analysis was designed with datas from the learning cohort. ROC curve revealed that the area under the curve was 0.974 (cf. FIG. 5B), what indicates that the test is strongly accurate in classifying cases as CMML or not CMML. ROC curve analysis reveals that a cutoff value of 93.9% of MO1 monocytes discriminates patient with CMML with a sensitivity of 95.6% and a specificity of 99%.

More precisely, FIG. 5 discloses the analysis of the MO1 population in learning and validation cohort.

The learning cohort is composed of young controls (n=232) and aged-match controls (n=26); other hemopathies group (n=16); Reactive monocytosis (n=32); CMML (n=43). The performance of MO1 percentage measurement assay in discriminating patients with CMML from those without CMML (controls, others hemopathies, reactive monocytosis) was evaluated. The area under the curve (AUC) is 0.974, suggesting that the test is strongly accurate in discriminate the two groups. ROC curve analysis reveals that a cutoff value of 93.9% of MO1 monocytes discriminates patient with CMML with a sensitivity of 95.6% and a specificity of 99%.

The validation cohort is composed of aged-match controls (n=67); patients with a myelodysplastic syndrome (MDS; n=28), patients with a reactive monocytosis (n=63); and CMML patients (n=28).

The results demonstrate that MO1 percentage in blood provides diagnostic accuracy in distinguishing CMML patients from those with monocytosis due to reactive monocytosis or associated with other hemopathies. These results were confirmed with the validation cohort included 186 blood samples (cf. FIG. 5C) and showed for the cutoff value of 93.9% of MO1 monocytes, a very strong discrimination of CMML patients with a sensitivity of 89.3% and a specificity of 92%.

Discriminant Value of the Ratio of Classical to Non-Classical Fraction (MO1/MO3)

As shown on FIG. 7A, the MO1/MO3 ratio was increased in CMML compared to all other tested cohorts (Kruskal-Wallis test, p<0.0001 for every subgroup compared to the CMML group in the learning cohort).

In the learning cohort, the use of the MO1/MO3 ratio to define CMML generated a ROC curve with an AUC of 0.967. The AUC of the ROC curve generated with MO1 percentage was 0.977, which was not statistically different (cf. FIG. 7B).

Altogether, the MO1/MO3 ratio is therefore also able to distinguish CMML from any other subgroup of healthy or diseased peoples, but is not more efficient than MO1 percentage.

Percentage of Classical Monocyte Subset as a Specific and Sensitive Tool for Monitoring the Sensitivity of a Subject having CMML to Treatments The analysis of MO1 percentage in blood in CMML patient under treatments (treatment by demethylating agents, azacitidin or decitabin) indicates if the patient is responder or not (cf. FIG. 6).

Percentage of Classical Monocyte Subset in Blood and Bone Marrow

Table 2 indicates that analysis of MO1 percentage by the gating strategy analysis by flow cytometry as tool for CMML diagnosis can be done with samples of whole blood or samples of bone marrow. Table 2 shows similar results of MO1 percentage in 12 patients.

| Sample | Whole blood MO1 % | Bone marrow MO1 % |
|---|---|---|
| 1 | 96.6 | 97.0 |
| 2 | 99.2 | 98.1 |
| 3 | 96.1 | 96.9 |
| 4 | 97.4 | 98.5 |
| 5 | 99.1 | 94.0 |
| 6 | 92.8 | 87.3 |
| 7 | 97.8 | 97.0 |
| 8 | 98.4 | 98.6 |
| 9 | 98.2 | 98.3 |
| 10 | 95.9 | 93.5 |
| 11 | 86.8 | 84.0 |
| 12 | 92.6 | 93.8 |

Table 2 shows MO1 percentage in whole blood and in bone morrow of the same 12 patients All the results set forth in the present application have been confirmed in a larger cohort of 307 patients (FIG. 7; data not shown).

The invention claimed is:

1. A method comprising the following steps in the order shown:
   a) obtaining a whole blood sample from a subject and diluting the sample to a concentration of total granulocytes under $10 \times 10^9$/L;
   b) contacting the diluted sample with antibodies labelled with fluorophores, wherein the labelled antibodies collectively recognize antigens expressed by granulocytes, T lymphocytes, B lymphocytes, and/or natural killer (NK) cells that are present in the sample;
   c) detecting by flow cytometry a monocyte cell population in the diluted sample, wherein the detecting step includes CD45+ cells but excludes CD2+ cells, CD56+ cells, CD15+ cells, CD16+ cells, and/or CD24+ cells that are present in the sample;
   d) quantifying by flow cytometry the $CD14^+/CD16^-$ monocytes in said diluted sample, quantifying total monocytes in said diluted sample, and calculating the ratio of $CD14^+/CD16^-$ monocytes to total monocytes; and
   e) diagnosing said subject as having chronic myelomonocytic leukemia (CMML) when the calculated ratio of $CD14^+/CD16^-$ monocytes to total monocytes in the diluted sample is higher than 0.936.

2. The method of claim 1, wherein said detecting step c) is performed by an exclusion gating strategy by flow cytometry.

3. The method of claim 1, wherein said monocytes in the diluted sample are $CD45^+$ cells, $CD15^-$ cells, $CD16^-$ cells, $CD2^-$ cells, $CD56^-$ cells, and/or $CD24^-$ cells.

4. The method of claim 1, further comprising:
   f) treating the subject for CMML based on the calculated ratio.

* * * * *

SEQUENCE LISTING

```
<160> NUMBER OF SEQ ID NOS: 9

<210> SEQ ID NO 1
<211> LENGTH: 375
<212> TYPE: PRT
<213> ORGANISM: homo sapiens
<220> FEATURE:
<221> NAME/KEY: MISC_FEATURE
<223> OTHER INFORMATION: amino acid sequence of human CD14

<400> SEQUENCE: 1

Met Glu Arg Ala Ser Cys Leu Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala
        35                  40                  45

Phe Gln Cys Val Ser Ala Val Glu Val Glu Ile His Ala Gly Gly Leu
    50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
            100                 105                 110

Leu Ala Tyr Ser Arg Leu Lys Glu Leu Thr Leu Glu Asp Leu Lys Ile
        115                 120                 125

Thr Gly Thr Met Pro Pro Leu Pro Leu Glu Ala Thr Gly Leu Ala Leu
    130                 135                 140
```

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
            165                 170                 175

Ile Ala Gln Ala His Ser Pro Ala Phe Ser Cys Glu Gln Val Arg Ala
            180                 185                 190

Phe Pro Ala Leu Thr Ser Leu Asp Leu Ser Asp Asn Pro Gly Leu Gly
            195                 200                 205

Glu Arg Gly Leu Met Ala Ala Leu Cys Pro His Lys Phe Pro Ala Ile
210                 215                 220

Gln Asn Leu Ala Leu Arg Asn Thr Gly Met Glu Thr Pro Thr Gly Val
225                 230                 235                 240

Cys Ala Ala Leu Ala Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
            275                 280                 285

Glu Gln Val Pro Lys Gly Leu Pro Ala Lys Leu Arg Val Leu Asp Leu
290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350

Ala Arg Ser Thr Leu Ser Val Gly Val Ser Gly Thr Leu Val Leu Leu
            355                 360                 365

Gln Gly Ala Arg Gly Phe Ala
            370                 375

<210> SEQ ID NO 2
<211> LENGTH: 290
<212> TYPE: PRT
<213> ORGANISM: homo sapiens
<220> FEATURE:
<221> NAME/KEY: MISC_FEATURE
<223> OTHER INFORMATION: amino acid sequence of human CD16 iso A

<400> SEQUENCE: 2

Met Gly Gly Gly Ala Gly Glu Arg Leu Phe Thr Ser Ser Cys Leu Val
1               5                   10                  15

Gly Leu Val Pro Leu Gly Leu Arg Ile Ser Leu Val Thr Cys Pro Leu
            20                  25                  30

Gln Cys Gly Ile Met Trp Gln Leu Leu Pro Thr Ala Leu Leu Leu
            35                  40                  45

Leu Val Ser Ala Gly Met Arg Thr Glu Asp Leu Pro Lys Ala Val Val
            50                  55                  60

Phe Leu Glu Pro Gln Trp Tyr Arg Val Leu Glu Lys Asp Ser Val Thr
65                  70                  75                  80

Leu Lys Cys Gln Gly Ala Tyr Ser Pro Glu Asp Asn Ser Thr Gln Trp
            85                  90                  95

Phe His Asn Glu Ser Leu Ile Ser Ser Gln Ala Ser Ser Tyr Phe Ile
            100                 105                 110

Asp Ala Ala Thr Val Asp Asp Ser Gly Glu Tyr Arg Cys Gln Thr Asn
            115                 120                 125

```
Leu Ser Thr Leu Ser Asp Pro Val Gln Leu Glu Val His Ile Gly Trp
        130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr
                165                 170                 175

Tyr Leu Gln Asn Gly Lys Gly Arg Lys Tyr Phe His His Asn Ser Asp
            180                 185                 190

Phe Tyr Ile Pro Lys Ala Thr Leu Lys Asp Ser Gly Ser Tyr Phe Cys
        195                 200                 205

Arg Gly Leu Phe Gly Ser Lys Asn Val Ser Ser Glu Thr Val Asn Ile
210                 215                 220

Thr Ile Thr Gln Gly Leu Ala Val Ser Thr Ile Ser Ser Phe Phe Pro
225                 230                 235                 240

Pro Gly Tyr Gln Val Ser Phe Cys Leu Val Met Val Leu Leu Phe Ala
                245                 250                 255

Val Asp Thr Gly Leu Tyr Phe Ser Val Lys Thr Asn Ile Arg Ser Ser
            260                 265                 270

Thr Arg Asp Trp Lys Asp His Lys Phe Lys Trp Arg Lys Asp Pro Gln
        275                 280                 285

Asp Lys
    290

<210> SEQ ID NO 3
<211> LENGTH: 269
<212> TYPE: PRT
<213> ORGANISM: homo sapiens
<220> FEATURE:
<221> NAME/KEY: MISC_FEATURE
<223> OTHER INFORMATION: amino acid sequence of human CD16 iso B

<400> SEQUENCE: 3

Met Gly Gly Gly Thr Gly Glu Arg Leu Phe Thr Pro Ser Cys Leu Val
1               5                   10                  15

Gly Leu Val Pro Leu Gly Leu Arg Ile Ser Leu Val Thr Cys Pro Leu
            20                  25                  30

Gln Cys Gly Ile Met Trp Gln Leu Leu Leu Pro Thr Ala Leu Leu Leu
        35                  40                  45

Leu Val Ser Ala Gly Met Arg Thr Glu Asp Leu Pro Lys Ala Val Val
    50                  55                  60

Phe Leu Glu Pro Gln Trp Tyr Ser Val Leu Glu Lys Asp Ser Val Thr
65                  70                  75                  80

Leu Lys Cys Gln Gly Ala Tyr Ser Pro Glu Asp Asn Ser Thr Gln Trp
                85                  90                  95

Phe His Asn Glu Asn Leu Ile Ser Ser Gln Ala Ser Ser Tyr Phe Ile
            100                 105                 110

Asp Ala Ala Thr Val Asn Asp Ser Gly Glu Tyr Arg Cys Gln Thr Asn
        115                 120                 125

Leu Ser Thr Leu Ser Asp Pro Val Gln Leu Glu Val His Ile Gly Trp
        130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr
                165                 170                 175

Tyr Leu Gln Asn Gly Lys Asp Arg Lys Tyr Phe His His Asn Ser Asp
```

```
                   180                 185                 190
Phe His Ile Pro Lys Ala Thr Leu Lys Asp Ser Gly Ser Tyr Phe Cys
            195                 200                 205

Arg Gly Leu Val Gly Ser Lys Asn Val Ser Ser Glu Thr Val Asn Ile
        210                 215                 220

Thr Ile Thr Gln Gly Leu Ala Val Ser Thr Ile Ser Ser Phe Ser Pro
225                 230                 235                 240

Pro Gly Tyr Gln Val Ser Phe Cys Leu Val Met Val Leu Leu Phe Ala
                245                 250                 255

Val Asp Thr Gly Leu Tyr Phe Ser Val Lys Thr Asn Ile
                260                 265
```

<210> SEQ ID NO 4
<211> LENGTH: 848
<212> TYPE: PRT
<213> ORGANISM: homo sapiens
<220> FEATURE:
<221> NAME/KEY: MISC_FEATURE
<223> OTHER INFORMATION: amino acid sequence of human CD56

<400> SEQUENCE: 4

```
Met Leu Gln Thr Lys Asp Leu Ile Trp Thr Leu Phe Phe Leu Gly Thr
1               5                  10                  15

Ala Val Ser Leu Gln Val Asp Ile Val Pro Ser Gln Gly Glu Ile Ser
            20                  25                  30

Val Gly Glu Ser Lys Phe Phe Leu Cys Gln Val Ala Gly Asp Ala Lys
        35                  40                  45

Asp Lys Asp Ile Ser Trp Phe Ser Pro Asn Gly Glu Lys Leu Thr Pro
    50                  55                  60

Asn Gln Gln Arg Ile Ser Val Val Trp Asn Asp Asp Ser Ser Ser Thr
65                  70                  75                  80

Leu Thr Ile Tyr Asn Ala Asn Ile Asp Asp Ala Gly Ile Tyr Lys Cys
                85                  90                  95

Val Val Thr Gly Glu Asp Gly Ser Glu Ser Glu Ala Thr Val Asn Val
            100                 105                 110

Lys Ile Phe Gln Lys Leu Met Phe Lys Asn Ala Pro Thr Pro Gln Glu
        115                 120                 125

Phe Arg Glu Gly Glu Asp Ala Val Ile Val Cys Asp Val Val Ser Ser
    130                 135                 140

Leu Pro Pro Thr Ile Ile Trp Lys His Lys Gly Arg Asp Val Ile Leu
145                 150                 155                 160

Lys Lys Asp Val Arg Phe Ile Val Leu Ser Asn Asn Tyr Leu Gln Ile
                165                 170                 175

Arg Gly Ile Lys Lys Thr Asp Glu Gly Thr Tyr Arg Cys Glu Gly Arg
            180                 185                 190

Ile Leu Ala Arg Gly Glu Ile Asn Phe Lys Asp Ile Gln Val Ile Val
        195                 200                 205

Asn Val Pro Pro Thr Ile Gln Ala Arg Gln Asn Ile Val Asn Ala Thr
    210                 215                 220

Ala Asn Leu Gly Gln Ser Val Thr Leu Val Cys Asp Ala Glu Gly Phe
225                 230                 235                 240

Pro Glu Pro Thr Met Ser Trp Thr Lys Asp Gly Glu Gln Ile Glu Gln
                245                 250                 255

Glu Glu Asp Asp Glu Lys Tyr Ile Phe Ser Asp Asp Ser Ser Gln Leu
            260                 265                 270
```

```
Thr Ile Lys Lys Val Asp Lys Asn Asp Glu Ala Glu Tyr Ile Cys Ile
            275                 280                 285
Ala Glu Asn Lys Ala Gly Glu Gln Asp Ala Thr Ile His Leu Lys Val
        290                 295                 300
Phe Ala Lys Pro Lys Ile Thr Tyr Val Glu Asn Gln Thr Ala Met Glu
305                 310                 315                 320
Leu Glu Glu Gln Val Thr Leu Thr Cys Glu Ala Ser Gly Asp Pro Ile
                    325                 330                 335
Pro Ser Ile Thr Trp Arg Thr Ser Thr Arg Asn Ile Ser Ser Glu Glu
            340                 345                 350
Lys Thr Leu Asp Gly His Met Val Val Arg Ser His Ala Arg Val Ser
        355                 360                 365
Ser Leu Thr Leu Lys Ser Ile Gln Tyr Thr Asp Ala Gly Glu Tyr Ile
    370                 375                 380
Cys Thr Ala Ser Asn Thr Ile Gly Gln Asp Ser Gln Ser Met Tyr Leu
385                 390                 395                 400
Glu Val Gln Tyr Ala Pro Lys Leu Gln Gly Pro Val Ala Val Tyr Thr
                    405                 410                 415
Trp Glu Gly Asn Gln Val Asn Ile Thr Cys Glu Val Phe Ala Tyr Pro
            420                 425                 430
Ser Ala Thr Ile Ser Trp Phe Arg Asp Gly Gln Leu Leu Pro Ser Ser
        435                 440                 445
Asn Tyr Ser Asn Ile Lys Ile Tyr Asn Thr Pro Ser Ala Ser Tyr Leu
    450                 455                 460
Glu Val Thr Pro Asp Ser Glu Asn Asp Phe Gly Asn Tyr Asn Cys Thr
465                 470                 475                 480
Ala Val Asn Arg Ile Gly Gln Glu Ser Leu Glu Phe Ile Leu Val Gln
                    485                 490                 495
Ala Asp Thr Pro Ser Ser Pro Ser Ile Asp Gln Val Glu Pro Tyr Ser
            500                 505                 510
Ser Thr Ala Gln Val Gln Phe Asp Glu Pro Glu Ala Thr Gly Gly Val
        515                 520                 525
Pro Ile Leu Lys Tyr Lys Ala Glu Trp Arg Ala Val Gly Glu Glu Val
    530                 535                 540
Trp His Ser Lys Trp Tyr Asp Ala Lys Glu Ala Ser Met Glu Gly Ile
545                 550                 555                 560
Val Thr Ile Val Gly Leu Lys Pro Glu Thr Thr Tyr Ala Val Arg Leu
                    565                 570                 575
Ala Ala Leu Asn Gly Lys Gly Leu Gly Glu Ile Ser Ala Ala Ser Glu
            580                 585                 590
Phe Lys Thr Gln Pro Val Gln Gly Glu Pro Ser Ala Pro Lys Leu Glu
        595                 600                 605
Gly Gln Met Gly Glu Asp Gly Asn Ser Ile Lys Val Asn Leu Ile Lys
    610                 615                 620
Gln Asp Asp Gly Gly Ser Pro Ile Arg His Tyr Leu Val Arg Tyr Arg
625                 630                 635                 640
Ala Leu Ser Ser Glu Trp Lys Pro Glu Ile Arg Leu Pro Ser Gly Ser
                    645                 650                 655
Asp His Val Met Leu Lys Ser Leu Asp Trp Asn Ala Glu Tyr Glu Val
            660                 665                 670
Tyr Val Val Ala Glu Asn Gln Gln Gly Lys Ser Lys Ala Ala His Phe
        675                 680                 685
Val Phe Arg Thr Ser Ala Gln Pro Thr Ala Ile Pro Ala Asn Gly Ser
```

```
            690                 695                 700
Pro Thr Ser Gly Leu Ser Thr Gly Ala Ile Val Gly Ile Leu Ile Val
705                 710                 715                 720

Ile Phe Val Leu Leu Val Val Asp Ile Thr Cys Tyr Phe Leu
                725                 730                 735

Asn Lys Cys Gly Leu Phe Met Cys Ile Ala Val Asn Leu Cys Gly Lys
                740                 745                 750

Ala Gly Pro Gly Ala Lys Gly Lys Asp Met Glu Glu Gly Lys Ala Ala
                755                 760                 765

Phe Ser Lys Asp Glu Ser Lys Glu Pro Ile Val Glu Val Arg Thr Glu
                770                 775                 780

Glu Glu Arg Thr Pro Asn His Asp Gly Gly Lys His Thr Glu Pro Asn
785                 790                 795                 800

Glu Thr Thr Pro Leu Thr Glu Pro Glu Lys Gly Pro Val Glu Ala Lys
                805                 810                 815

Pro Glu Cys Gln Glu Thr Glu Thr Lys Pro Ala Pro Ala Glu Val Lys
                820                 825                 830

Thr Val Pro Asn Asp Ala Thr Gln Thr Lys Glu Asn Glu Ser Lys Ala
                835                 840                 845

<210> SEQ ID NO 5
<211> LENGTH: 351
<212> TYPE: PRT
<213> ORGANISM: homo sapiens
<220> FEATURE:
<221> NAME/KEY: MISC_FEATURE
<223> OTHER INFORMATION: amino acid sequence of human CD2

<400> SEQUENCE: 5

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
                20                  25                  30

Thr Trp Gly Ala Leu Gly Gln Asp Ile Asn Leu Asp Ile Pro Ser Phe
            35                  40                  45

Gln Met Ser Asp Asp Ile Asp Asp Ile Lys Trp Glu Lys Thr Ser Asp
        50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
                100                 105                 110

Lys Gly Lys Asn Val Leu Glu Lys Ile Phe Asp Leu Lys Ile Gln Glu
                115                 120                 125

Arg Val Ser Lys Pro Lys Ile Ser Trp Thr Cys Ile Asn Thr Thr Leu
130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
                180                 185                 190

Ser Lys Glu Ser Ser Val Glu Pro Val Ser Cys Pro Glu Lys Gly Leu
                195                 200                 205
```

```
Asp Ile Tyr Leu Ile Ile Gly Ile Cys Gly Gly Ser Leu Leu Met
        210                 215                 220

Val Phe Val Ala Leu Leu Val Phe Tyr Ile Thr Lys Arg Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
            260                 265                 270

Pro Gln Asn Pro Ala Thr Ser Gln His Pro Pro Pro Pro Gly His
                275                 280                 285

Arg Ser Gln Ala Pro Ser His Arg Pro Pro Pro Gly His Arg Val
290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Ser Asn
                340                 345                 350
```

<210> SEQ ID NO 6
<211> LENGTH: 80
<212> TYPE: PRT
<213> ORGANISM: homo sapiens
<220> FEATURE:
<221> NAME/KEY: MISC_FEATURE
<223> OTHER INFORMATION: amino acid sequence of human CD24

<400> SEQUENCE: 6

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
            35                  40                  45

Asn Pro Thr Asn Ala Thr Thr Lys Ala Ala Gly Gly Ala Leu Gln Ser
        50                  55                  60

Thr Ala Ser Leu Phe Val Val Ser Leu Ser Leu Leu His Leu Tyr Ser
65                  70                  75                  80
```

<210> SEQ ID NO 7
<211> LENGTH: 1306
<212> TYPE: PRT
<213> ORGANISM: homo sapiens
<220> FEATURE:
<221> NAME/KEY: MISC_FEATURE
<223> OTHER INFORMATION: amino acid sequence of human CD45 iso 1

<400> SEQUENCE: 7

```
Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
                20                  25                  30

Thr Gly Leu Thr Thr Ala Lys Met Pro Ser Val Pro Leu Ser Ser Asp
            35                  40                  45

Pro Leu Pro Thr His Thr Thr Ala Phe Ser Pro Ala Ser Thr Phe Glu
        50                  55                  60

Arg Glu Asn Asp Phe Ser Glu Thr Thr Thr Ser Leu Ser Pro Asp Asn
65                  70                  75                  80
```

```
Thr Ser Thr Gln Val Ser Pro Asp Ser Leu Asp Asn Ala Ser Ala Phe
            85              90              95
Asn Thr Thr Gly Val Ser Val Gln Thr Pro His Leu Pro Thr His
            100             105             110
Ala Asp Ser Gln Thr Pro Ser Ala Gly Thr Asp Thr Gln Thr Phe Ser
            115             120             125
Gly Ser Ala Ala Asn Ala Lys Leu Asn Pro Thr Pro Gly Ser Asn Ala
            130             135             140
Ile Ser Asp Val Pro Gly Glu Arg Ser Thr Ala Ser Thr Phe Pro Thr
145             150             155             160
Asp Pro Val Ser Pro Leu Thr Thr Thr Leu Ser Leu Ala His His Ser
                165             170             175
Ser Ala Ala Leu Pro Ala Arg Thr Ser Asn Thr Thr Ile Thr Ala Asn
            180             185             190
Thr Ser Asp Ala Tyr Leu Asn Ala Ser Glu Thr Thr Thr Leu Ser Pro
            195             200             205
Ser Gly Ser Ala Val Ile Ser Thr Thr Thr Ile Ala Thr Thr Pro Ser
            210             215             220
Lys Pro Thr Cys Asp Glu Lys Tyr Ala Asn Ile Thr Val Asp Tyr Leu
225             230             235             240
Tyr Asn Lys Glu Thr Lys Leu Phe Thr Ala Lys Leu Asn Val Asn Glu
                245             250             255
Asn Val Glu Cys Gly Asn Asn Thr Cys Thr Asn Asn Glu Val His Asn
                260             265             270
Leu Thr Glu Cys Lys Asn Ala Ser Val Ser Ile Ser His Asn Ser Cys
            275             280             285
Thr Ala Pro Asp Lys Thr Leu Ile Leu Asp Val Pro Pro Gly Val Glu
            290             295             300
Lys Phe Gln Leu His Asp Cys Thr Gln Val Glu Lys Ala Asp Thr Thr
305             310             315             320
Ile Cys Leu Lys Trp Lys Asn Ile Glu Thr Phe Thr Cys Asp Thr Gln
                325             330             335
Asn Ile Thr Tyr Arg Phe Gln Cys Gly Asn Met Ile Phe Asp Asn Lys
            340             345             350
Glu Ile Lys Leu Glu Asn Leu Glu Pro Glu His Glu Tyr Lys Cys Asp
            355             360             365
Ser Glu Ile Leu Tyr Asn Asn His Lys Phe Thr Asn Ala Ser Lys Ile
            370             375             380
Ile Lys Thr Asp Phe Gly Ser Pro Gly Glu Pro Gln Ile Ile Phe Cys
385             390             395             400
Arg Ser Glu Ala Ala His Gln Gly Val Ile Thr Trp Asn Pro Pro Gln
            405             410             415
Arg Ser Phe His Asn Phe Thr Leu Cys Tyr Ile Lys Glu Thr Glu Lys
            420             425             430
Asp Cys Leu Asn Leu Asp Lys Asn Leu Ile Lys Tyr Asp Leu Gln Asn
            435             440             445
Leu Lys Pro Tyr Thr Lys Tyr Val Leu Ser Leu His Ala Tyr Ile Ile
450             455             460
Ala Lys Val Gln Arg Asn Gly Ser Ala Ala Met Cys His Phe Thr Thr
465             470             475             480
Lys Ser Ala Pro Pro Ser Gln Val Trp Asn Met Thr Val Ser Met Thr
            485             490             495
Ser Asp Asn Ser Met His Val Lys Cys Arg Pro Pro Arg Asp Arg Asn
```

```
                500                 505                 510
Gly Pro His Glu Arg Tyr His Leu Glu Val Glu Ala Gly Asn Thr Leu
            515                 520                 525

Val Arg Asn Glu Ser His Lys Asn Cys Asp Phe Arg Val Lys Asp Leu
530                 535                 540

Gln Tyr Ser Thr Asp Tyr Thr Phe Lys Ala Tyr Phe His Asn Gly Asp
545                 550                 555                 560

Tyr Pro Gly Glu Pro Phe Ile Leu His His Ser Thr Ser Tyr Asn Ser
            565                 570                 575

Lys Ala Leu Ile Ala Phe Leu Ala Phe Leu Ile Val Thr Ser Ile
            580                 585                 590

Ala Leu Leu Val Val Leu Tyr Lys Ile Tyr Asp Leu His Lys Lys Arg
            595                 600                 605

Ser Cys Asn Leu Asp Glu Gln Gln Glu Leu Val Glu Arg Asp Asp Glu
            610                 615                 620

Lys Gln Leu Met Asn Val Glu Pro Ile His Ala Asp Ile Leu Leu Glu
625                 630                 635                 640

Thr Tyr Lys Arg Lys Ile Ala Asp Glu Gly Arg Leu Phe Leu Ala Glu
            645                 650                 655

Phe Gln Ser Ile Pro Arg Val Phe Ser Lys Phe Pro Ile Lys Glu Ala
            660                 665                 670

Arg Lys Pro Phe Asn Gln Asn Lys Asn Arg Tyr Val Asp Ile Leu Pro
            675                 680                 685

Tyr Asp Tyr Asn Arg Val Glu Leu Ser Glu Ile Asn Gly Asp Ala Gly
            690                 695                 700

Ser Asn Tyr Ile Asn Ala Ser Tyr Ile Asp Gly Phe Lys Glu Pro Arg
705                 710                 715                 720

Lys Tyr Ile Ala Ala Gln Gly Pro Arg Asp Glu Thr Val Asp Asp Phe
            725                 730                 735

Trp Arg Met Ile Trp Glu Gln Lys Ala Thr Val Ile Val Met Val Thr
            740                 745                 750

Arg Cys Glu Glu Gly Asn Arg Asn Lys Cys Ala Glu Tyr Trp Pro Ser
            755                 760                 765

Met Glu Glu Gly Thr Arg Ala Phe Gly Asp Val Val Val Lys Ile Asn
            770                 775                 780

Gln His Lys Arg Cys Pro Asp Tyr Ile Ile Gln Lys Leu Asn Ile Val
785                 790                 795                 800

Asn Lys Lys Glu Lys Ala Thr Gly Arg Glu Val Thr His Ile Gln Phe
            805                 810                 815

Thr Ser Trp Pro Asp His Gly Val Pro Glu Asp Pro His Leu Leu Leu
            820                 825                 830

Lys Leu Arg Arg Arg Val Asn Ala Phe Ser Asn Phe Phe Ser Gly Pro
            835                 840                 845

Ile Val Val His Cys Ser Ala Gly Val Gly Arg Thr Gly Thr Tyr Ile
            850                 855                 860

Gly Ile Asp Ala Met Leu Glu Gly Leu Glu Ala Glu Asn Lys Val Asp
865                 870                 875                 880

Val Tyr Gly Tyr Val Val Lys Leu Arg Arg Gln Arg Cys Leu Met Val
            885                 890                 895

Gln Val Glu Ala Gln Tyr Ile Leu Ile His Gln Ala Leu Val Glu Tyr
            900                 905                 910

Asn Gln Phe Gly Glu Thr Glu Val Asn Leu Ser Glu Leu His Pro Tyr
            915                 920                 925
```

-continued

Leu His Asn Met Lys Lys Arg Asp Pro Pro Ser Glu Pro Ser Pro Leu
            930                 935                 940

Glu Ala Glu Phe Gln Arg Leu Pro Ser Tyr Arg Ser Trp Arg Thr Gln
945                 950                 955                 960

His Ile Gly Asn Gln Glu Glu Asn Lys Ser Lys Asn Arg Asn Ser Asn
                965                 970                 975

Val Ile Pro Tyr Asp Tyr Asn Arg Val Pro Leu Lys His Glu Leu Glu
            980                 985                 990

Met Ser Lys Glu Ser Glu His Asp Ser Asp Glu Ser Ser Asp Asp Asp
        995                 1000                1005

Ser Asp Ser Glu Glu Pro Ser Lys Tyr Ile Asn Ala Ser Phe Ile
    1010                1015                1020

Met Ser Tyr Trp Lys Pro Glu Val Met Ile Ala Ala Gln Gly Pro
    1025                1030                1035

Leu Lys Glu Thr Ile Gly Asp Phe Trp Gln Met Ile Phe Gln Arg
    1040                1045                1050

Lys Val Lys Val Ile Val Met Leu Thr Glu Leu Lys His Gly Asp
    1055                1060                1065

Gln Glu Ile Cys Ala Gln Tyr Trp Gly Glu Gly Lys Gln Thr Tyr
    1070                1075                1080

Gly Asp Ile Glu Val Asp Leu Lys Asp Thr Asp Lys Ser Ser Thr
    1085                1090                1095

Tyr Thr Leu Arg Val Phe Glu Leu Arg His Ser Lys Arg Lys Asp
    1100                1105                1110

Ser Arg Thr Val Tyr Gln Tyr Gln Tyr Thr Asn Trp Ser Val Glu
    1115                1120                1125

Gln Leu Pro Ala Glu Pro Lys Glu Leu Ile Ser Met Ile Gln Val
    1130                1135                1140

Val Lys Gln Lys Leu Pro Gln Lys Asn Ser Ser Glu Gly Asn Lys
    1145                1150                1155

His His Lys Ser Thr Pro Leu Leu Ile His Cys Arg Asp Gly Ser
    1160                1165                1170

Gln Gln Thr Gly Ile Phe Cys Ala Leu Leu Asn Leu Leu Glu Ser
    1175                1180                1185

Ala Glu Thr Glu Glu Val Val Asp Ile Phe Gln Val Val Lys Ala
    1190                1195                1200

Leu Arg Lys Ala Arg Pro Gly Met Val Ser Thr Phe Glu Gln Tyr
    1205                1210                1215

Gln Phe Leu Tyr Asp Val Ile Ala Ser Thr Tyr Pro Ala Gln Asn
    1220                1225                1230

Gly Gln Val Lys Lys Asn Asn His Gln Glu Asp Lys Ile Glu Phe
    1235                1240                1245

Asp Asn Glu Val Asp Lys Val Lys Gln Asp Ala Asn Cys Val Asn
    1250                1255                1260

Pro Leu Gly Ala Pro Glu Lys Leu Pro Glu Ala Lys Glu Gln Ala
    1265                1270                1275

Glu Gly Ser Glu Pro Thr Ser Gly Thr Glu Gly Pro Glu His Ser
    1280                1285                1290

Val Asn Gly Pro Ala Ser Pro Ala Leu Asn Gln Gly Ser
    1295                1300                1305

<210> SEQ ID NO 8
<211> LENGTH: 1145

```
<212> TYPE: PRT
<213> ORGANISM: homo sapiens
<220> FEATURE:
<221> NAME/KEY: MISC_FEATURE
<223> OTHER INFORMATION: amino acid sequence of human CD45 iso 2

<400> SEQUENCE: 8
```

| | | | | | | | | | | | | | | |
|---|---|---|---|---|---|---|---|---|---|---|---|---|---|---|
| Met | Thr | Met | Tyr | Leu | Trp | Leu | Lys | Leu | Leu | Ala | Phe | Gly | Phe | Ala | Phe |
| 1 | | | | 5 | | | | | 10 | | | | | 15 | |
| Leu | Asp | Thr | Glu | Val | Phe | Val | Thr | Gly | Gln | Ser | Pro | Thr | Pro | Ser | Pro |
| | | | 20 | | | | | 25 | | | | | 30 | | |
| Thr | Asp | Ala | Tyr | Leu | Asn | Ala | Ser | Glu | Thr | Thr | Thr | Leu | Ser | Pro | Ser |
| | | 35 | | | | | 40 | | | | | 45 | | | |
| Gly | Ser | Ala | Val | Ile | Ser | Thr | Thr | Thr | Ile | Ala | Thr | Thr | Pro | Ser | Lys |
| | 50 | | | | | 55 | | | | | 60 | | | | |
| Pro | Thr | Cys | Asp | Glu | Lys | Tyr | Ala | Asn | Ile | Thr | Val | Asp | Tyr | Leu | Tyr |
| 65 | | | | | 70 | | | | | 75 | | | | | 80 |
| Asn | Lys | Glu | Thr | Lys | Leu | Phe | Thr | Ala | Lys | Leu | Asn | Val | Asn | Glu | Asn |
| | | | | 85 | | | | | 90 | | | | | 95 | |
| Val | Glu | Cys | Gly | Asn | Asn | Thr | Cys | Thr | Asn | Asn | Glu | Val | His | Asn | Leu |
| | | | 100 | | | | | 105 | | | | | 110 | | |
| Thr | Glu | Cys | Lys | Asn | Ala | Ser | Val | Ser | Ile | Ser | His | Asn | Ser | Cys | Thr |
| | | 115 | | | | | 120 | | | | | 125 | | | |
| Ala | Pro | Asp | Lys | Thr | Leu | Ile | Leu | Asp | Val | Pro | Pro | Gly | Val | Glu | Lys |
| | 130 | | | | | 135 | | | | | 140 | | | | |
| Phe | Gln | Leu | His | Asp | Cys | Thr | Gln | Val | Glu | Lys | Ala | Asp | Thr | Thr | Ile |
| 145 | | | | | 150 | | | | | 155 | | | | | 160 |
| Cys | Leu | Lys | Trp | Lys | Asn | Ile | Glu | Thr | Phe | Thr | Cys | Asp | Thr | Gln | Asn |
| | | | | 165 | | | | | 170 | | | | | 175 | |
| Ile | Thr | Tyr | Arg | Phe | Gln | Cys | Gly | Asn | Met | Ile | Phe | Asp | Asn | Lys | Glu |
| | | | 180 | | | | | 185 | | | | | 190 | | |
| Ile | Lys | Leu | Glu | Asn | Leu | Glu | Pro | Glu | His | Glu | Tyr | Lys | Cys | Asp | Ser |
| | | 195 | | | | | 200 | | | | | 205 | | | |
| Glu | Ile | Leu | Tyr | Asn | Asn | His | Lys | Phe | Thr | Asn | Ala | Ser | Lys | Ile | Ile |
| | 210 | | | | | 215 | | | | | 220 | | | | |
| Lys | Thr | Asp | Phe | Gly | Ser | Pro | Gly | Glu | Pro | Gln | Ile | Ile | Phe | Cys | Arg |
| 225 | | | | | 230 | | | | | 235 | | | | | 240 |
| Ser | Glu | Ala | Ala | His | Gln | Gly | Val | Ile | Thr | Trp | Asn | Pro | Pro | Gln | Arg |
| | | | | 245 | | | | | 250 | | | | | 255 | |
| Ser | Phe | His | Asn | Phe | Thr | Leu | Cys | Tyr | Ile | Lys | Glu | Thr | Glu | Lys | Asp |
| | | | 260 | | | | | 265 | | | | | 270 | | |
| Cys | Leu | Asn | Leu | Asp | Lys | Asn | Leu | Ile | Lys | Tyr | Asp | Leu | Gln | Asn | Leu |
| | | 275 | | | | | 280 | | | | | 285 | | | |
| Lys | Pro | Tyr | Thr | Lys | Tyr | Val | Leu | Ser | Leu | His | Ala | Tyr | Ile | Ile | Ala |
| | 290 | | | | | 295 | | | | | 300 | | | | |
| Lys | Val | Gln | Arg | Asn | Gly | Ser | Ala | Ala | Met | Cys | His | Phe | Thr | Thr | Lys |
| 305 | | | | | 310 | | | | | 315 | | | | | 320 |
| Ser | Ala | Pro | Pro | Ser | Gln | Val | Trp | Asn | Met | Thr | Val | Ser | Met | Thr | Ser |
| | | | | 325 | | | | | 330 | | | | | 335 | |
| Asp | Asn | Ser | Met | His | Val | Lys | Cys | Arg | Pro | Pro | Arg | Asp | Arg | Asn | Gly |
| | | | 340 | | | | | 345 | | | | | 350 | | |
| Pro | His | Glu | Arg | Tyr | His | Leu | Glu | Val | Glu | Ala | Gly | Asn | Thr | Leu | Val |
| | | 355 | | | | | 360 | | | | | 365 | | | |
| Arg | Asn | Glu | Ser | His | Lys | Asn | Cys | Asp | Phe | Arg | Val | Lys | Asp | Leu | Gln |
| | 370 | | | | | 375 | | | | | 380 | | | | |

```
Tyr Ser Thr Asp Tyr Thr Phe Lys Ala Tyr Phe His Asn Gly Asp Tyr
385                 390                 395                 400

Pro Gly Glu Pro Phe Ile Leu His His Ser Thr Ser Tyr Asn Ser Lys
            405                 410                 415

Ala Leu Ile Ala Phe Leu Ala Phe Leu Ile Ile Val Thr Ser Ile Ala
        420                 425                 430

Leu Leu Val Val Leu Tyr Lys Ile Tyr Asp Leu His Lys Lys Arg Ser
            435                 440                 445

Cys Asn Leu Asp Glu Gln Gln Glu Leu Val Glu Arg Asp Asp Glu Lys
        450                 455                 460

Gln Leu Met Asn Val Glu Pro Ile His Ala Asp Ile Leu Leu Glu Thr
465                 470                 475                 480

Tyr Lys Arg Lys Ile Ala Asp Glu Gly Arg Leu Phe Leu Ala Glu Phe
            485                 490                 495

Gln Ser Ile Pro Arg Val Phe Ser Lys Phe Pro Ile Lys Glu Ala Arg
            500                 505                 510

Lys Pro Phe Asn Gln Asn Lys Asn Arg Tyr Val Asp Ile Leu Pro Tyr
            515                 520                 525

Asp Tyr Asn Arg Val Glu Leu Ser Glu Ile Asn Gly Asp Ala Gly Ser
530                 535                 540

Asn Tyr Ile Asn Ala Ser Tyr Ile Asp Gly Phe Lys Glu Pro Arg Lys
545                 550                 555                 560

Tyr Ile Ala Ala Gln Gly Pro Arg Asp Glu Thr Val Asp Asp Phe Trp
            565                 570                 575

Arg Met Ile Trp Glu Gln Lys Ala Thr Val Ile Val Met Val Thr Arg
            580                 585                 590

Cys Glu Glu Gly Asn Arg Asn Lys Cys Ala Glu Tyr Trp Pro Ser Met
        595                 600                 605

Glu Glu Gly Thr Arg Ala Phe Gly Asp Val Val Lys Ile Asn Gln
        610                 615                 620

His Lys Arg Cys Pro Asp Tyr Ile Ile Gln Lys Leu Asn Ile Val Asn
625                 630                 635                 640

Lys Lys Glu Lys Ala Thr Gly Arg Glu Val Thr His Ile Gln Phe Thr
            645                 650                 655

Ser Trp Pro Asp His Gly Val Pro Glu Asp Pro His Leu Leu Leu Lys
        660                 665                 670

Leu Arg Arg Arg Val Asn Ala Phe Ser Asn Phe Phe Ser Gly Pro Ile
        675                 680                 685

Val Val His Cys Ser Ala Gly Val Gly Arg Thr Gly Thr Tyr Ile Gly
        690                 695                 700

Ile Asp Ala Met Leu Glu Gly Leu Glu Ala Glu Asn Lys Val Asp Val
705                 710                 715                 720

Tyr Gly Tyr Val Val Lys Leu Arg Arg Gln Arg Cys Leu Met Val Gln
            725                 730                 735

Val Glu Ala Gln Tyr Ile Leu Ile His Gln Ala Leu Val Glu Tyr Asn
            740                 745                 750

Gln Phe Gly Glu Thr Glu Val Asn Leu Ser Glu Leu His Pro Tyr Leu
        755                 760                 765

His Asn Met Lys Lys Arg Asp Pro Pro Ser Glu Pro Ser Pro Leu Glu
        770                 775                 780

Ala Glu Phe Gln Arg Leu Pro Ser Tyr Arg Ser Trp Arg Thr Gln His
785                 790                 795                 800
```

Ile Gly Asn Gln Glu Glu Asn Lys Ser Lys Asn Arg Asn Ser Asn Val
                805                 810                 815

Ile Pro Tyr Asp Tyr Asn Arg Val Pro Leu Lys His Glu Leu Glu Met
        820                 825                 830

Ser Lys Glu Ser Glu His Asp Ser Asp Glu Ser Ser Asp Asp Asp Ser
            835                 840                 845

Asp Ser Glu Glu Pro Ser Lys Tyr Ile Asn Ala Ser Phe Ile Met Ser
850                 855                 860

Tyr Trp Lys Pro Glu Val Met Ile Ala Ala Gln Gly Pro Leu Lys Glu
865                 870                 875                 880

Thr Ile Gly Asp Phe Trp Gln Met Ile Phe Gln Arg Lys Val Lys Val
                885                 890                 895

Ile Val Met Leu Thr Glu Leu Lys His Gly Asp Gln Glu Ile Cys Ala
            900                 905                 910

Gln Tyr Trp Gly Glu Gly Lys Gln Thr Tyr Gly Asp Ile Glu Val Asp
        915                 920                 925

Leu Lys Asp Thr Asp Lys Ser Ser Thr Tyr Thr Leu Arg Val Phe Glu
930                 935                 940

Leu Arg His Ser Lys Arg Lys Asp Ser Arg Thr Val Tyr Gln Tyr Gln
945                 950                 955                 960

Tyr Thr Asn Trp Ser Val Glu Gln Leu Pro Ala Glu Pro Lys Glu Leu
                965                 970                 975

Ile Ser Met Ile Gln Val Val Lys Gln Lys Leu Pro Gln Lys Asn Ser
            980                 985                 990

Ser Glu Gly Asn Lys His His Lys Ser Thr Pro Leu Leu Ile His Cys
        995                 1000                1005

Arg Asp Gly Ser Gln Gln Thr Gly Ile Phe Cys Ala Leu Leu Asn
    1010                1015                1020

Leu Leu Glu Ser Ala Glu Thr Glu Glu Val Val Asp Ile Phe Gln
    1025                1030                1035

Val Val Lys Ala Leu Arg Lys Ala Arg Pro Gly Met Val Ser Thr
    1040                1045                1050

Phe Glu Gln Tyr Gln Phe Leu Tyr Asp Val Ile Ala Ser Thr Tyr
    1055                1060                1065

Pro Ala Gln Asn Gly Gln Val Lys Lys Asn Asn His Gln Glu Asp
    1070                1075                1080

Lys Ile Glu Phe Asp Asn Glu Val Asp Lys Val Lys Gln Asp Ala
    1085                1090                1095

Asn Cys Val Asn Pro Leu Gly Ala Pro Glu Lys Leu Pro Glu Ala
    1100                1105                1110

Lys Glu Gln Ala Glu Gly Ser Glu Pro Thr Ser Gly Thr Glu Gly
    1115                1120                1125

Pro Glu His Ser Val Asn Gly Pro Ala Ser Pro Ala Leu Asn Gln
    1130                1135                1140

Gly Ser
    1145

<210> SEQ ID NO 9
<211> LENGTH: 530
<212> TYPE: PRT
<213> ORGANISM: homo sapiens
<220> FEATURE:
<221> NAME/KEY: MISC_FEATURE
<223> OTHER INFORMATION: CD15

<400> SEQUENCE: 9

-continued

Met Arg Arg Leu Trp Gly Ala Ala Arg Lys Pro Ser Gly Ala Gly Trp
1               5                   10                  15

Glu Lys Glu Trp Ala Glu Ala Pro Gln Glu Ala Pro Gly Ala Trp Ser
            20                  25                  30

Gly Arg Leu Gly Pro Gly Arg Ser Gly Arg Lys Gly Arg Ala Val Pro
        35                  40                  45

Gly Trp Ala Ser Trp Pro Ala His Leu Ala Leu Ala Ala Arg Pro Ala
    50                  55                  60

Arg His Leu Gly Gly Ala Gly Gln Gly Pro Arg Pro Leu His Ser Gly
65                  70                  75                  80

Thr Ala Pro Phe His Ser Arg Ala Ser Gly Glu Arg Gln Arg Arg Leu
                85                  90                  95

Glu Pro Gln Leu Gln His Glu Ser Arg Cys Arg Ser Ser Thr Pro Ala
            100                 105                 110

Asp Ala Trp Arg Ala Glu Ala Ala Leu Pro Val Arg Ala Met Gly Ala
        115                 120                 125

Pro Trp Gly Ser Pro Thr Ala Ala Gly Gly Arg Arg Gly Trp Arg
    130                 135                 140

Arg Gly Arg Gly Leu Pro Trp Thr Val Cys Val Leu Ala Ala Ala Gly
145                 150                 155                 160

Leu Thr Cys Thr Ala Leu Ile Thr Tyr Ala Cys Trp Gly Gln Leu Pro
                165                 170                 175

Pro Leu Pro Trp Ala Ser Pro Thr Pro Ser Arg Pro Val Gly Val Leu
            180                 185                 190

Leu Trp Trp Glu Pro Phe Gly Gly Arg Asp Ser Ala Pro Arg Pro Pro
        195                 200                 205

Pro Asp Cys Arg Leu Arg Phe Asn Ile Ser Gly Cys Arg Leu Leu Thr
210                 215                 220

Asp Arg Ala Ser Tyr Gly Glu Ala Gln Ala Val Leu Phe His His Arg
225                 230                 235                 240

Asp Leu Val Lys Gly Pro Pro Asp Trp Pro Pro Trp Gly Ile Gln
                245                 250                 255

Ala His Thr Ala Glu Glu Val Asp Leu Arg Val Leu Asp Tyr Glu Glu
            260                 265                 270

Ala Ala Ala Ala Ala Glu Ala Leu Ala Thr Ser Ser Pro Arg Pro Pro
        275                 280                 285

Gly Gln Arg Trp Val Trp Met Asn Phe Glu Ser Pro Ser His Ser Pro
    290                 295                 300

Gly Leu Arg Ser Leu Ala Ser Asn Leu Phe Asn Trp Thr Leu Ser Tyr
305                 310                 315                 320

Arg Ala Asp Ser Asp Val Phe Val Pro Tyr Gly Tyr Leu Tyr Pro Arg
                325                 330                 335

Ser His Pro Gly Asp Pro Pro Ser Gly Leu Ala Pro Leu Ser Arg
            340                 345                 350

Lys Gln Gly Leu Val Ala Trp Val Ser His Trp Asp Glu Arg Gln
        355                 360                 365

Ala Arg Val Arg Tyr Tyr His Gln Leu Ser Gln His Val Thr Val Asp
    370                 375                 380

Val Phe Gly Arg Gly Gly Pro Gly Gln Pro Val Pro Glu Ile Gly Leu
385                 390                 395                 400

Leu His Thr Val Ala Arg Tyr Lys Phe Tyr Leu Ala Phe Glu Asn Ser
                405                 410                 415

-continued

```
Gln His Leu Asp Tyr Ile Thr Glu Lys Leu Trp Arg Asn Ala Leu Leu
            420             425                 430

Ala Gly Ala Val Pro Val Val Leu Gly Pro Asp Arg Ala Asn Tyr Glu
        435             440                 445

Arg Phe Val Pro Arg Gly Ala Phe Ile His Val Asp Asp Phe Pro Ser
        450             455             460

Ala Ser Ser Leu Ala Ser Tyr Leu Leu Phe Leu Asp Arg Asn Pro Ala
465             470                 475                     480

Val Tyr Arg Arg Tyr Phe His Trp Arg Arg Ser Tyr Ala Val His Ile
                485             490                     495

Thr Ser Phe Trp Asp Glu Pro Trp Cys Arg Val Cys Gln Ala Val Gln
            500             505             510

Arg Ala Gly Asp Arg Pro Lys Ser Ile Arg Asn Leu Ala Ser Trp Phe
        515             520             525

Glu Arg
    530
```